United States Patent [19]
Downs

[11] Patent Number: 5,546,184
[45] Date of Patent: Aug. 13, 1996

[54] SINGLE-FREQUENCY BIDIRECTIONAL FRINGE-COUNTING INTERFEROMETER

[75] Inventor: Michael J. Downs, Liphook, England

[73] Assignee: British Technology Group Ltd., London, England

[21] Appl. No.: 232,280

[22] PCT Filed: Nov. 5, 1992

[86] PCT No.: PCT/GB92/02042

§ 371 Date: May 6, 1994

§ 102(e) Date: May 6, 1994

[87] PCT Pub. No.: WO93/09394

PCT Pub. Date: May 13, 1993

[30] Foreign Application Priority Data

Nov. 8, 1991 [GB] United Kingdom ............... 9123785
Oct. 15, 1992 [GB] United Kingdom ............... 9221698

[51] Int. Cl.[6] ............................................. G01B 9/02
[52] U.S. Cl. ............................................. 356/345; 356/346
[58] Field of Search ...................... 356/345, 351, 356/361, 358, 346

[56] References Cited

U.S. PATENT DOCUMENTS

| | | | |
|---|---|---|---|
| 1,770,355 | 7/1930 | Downs | 356/361 |
| 2,795,991 | 6/1957 | Tuzi | 356/361 |
| 4,027,976 | 6/1977 | Amon . | |
| 4,180,703 | 12/1979 | Cialone et al. . | |
| 4,693,605 | 9/1987 | Sommargren | 356/351 |
| 5,076,695 | 12/1991 | Ichihara . | |
| 5,148,318 | 9/1992 | Okamoto et al. | 359/629 |

FOREIGN PATENT DOCUMENTS

| | | |
|---|---|---|
| 0006441 | 1/1980 | European Pat. Off. . |
| 2271539 | 12/1975 | France . |
| 2123667 | 2/1972 | Germany . |
| 1104081 | 2/1968 | United Kingdom . |
| 1176019 | 1/1970 | United Kingdom . |
| 1244337 | 8/1971 | United Kingdom . |
| 1343636 | 1/1974 | United Kingdom . |
| 2079000 | 1/1982 | United Kingdom . |
| 2086039 | 5/1982 | United Kingdom . |
| 2109545 | 6/1983 | United Kingdom . |
| 2235789 | 3/1991 | United Kingdom . |
| 2236181 | 3/1991 | United Kingdom . |

OTHER PUBLICATIONS

Instruments and Experimental Technques vol. 20, No. 4, 7 Aug. 1977, New York US, pp. 1151–1153.
V. G. Vyskub E. A. "Beam Splitter with 90° Phase Shift For Interference Displacement . . . " pp. 1151–1152.
Technisches Messen TM, vol. 58, No. 4 Apr. 1991, Muchen DE, pp. 146–151, XP227766, G. Ulbergs "Integriert–Optische Sensoren Fur Die Weg–", Kraft–Und.
Mesures Regulation Automatisme, vol. 47, No. 5, May 1982, Paris FR, pp. 7–26 Raymond Boult "Lasers: A Chacun Son Application" See FIG. 13.
Optical Engineering, vol. 27, No. 19, 1 Sep. 1988, Bellingham US, pp. 823–829, S. Mori E. A. "Laser Measurement System for Precise and Fast Positioning".
F. A. Jenkins & I H. E. White, "Fundamentals of Optics", 1957, McGraw-Hill, pp. 245, 274, 520, 523, 524.

*Primary Examiner*—Samuel A. Turner
*Attorney, Agent, or Firm*—Cushman Darby & Cushman

[57] ABSTRACT

An optical interferometer includes a beam splitter 131 having a partially reflecting metallic film 135, 137 adapted to induce phase difference between the transmitted and reflected component beams. It incorporates bidirectional fringe counter which includes a switching circuit to convert coupling with the fringe counter means from ac coupling to dc coupling when the counting rate falls below a predetermined threshold value.

21 Claims, 18 Drawing Sheets

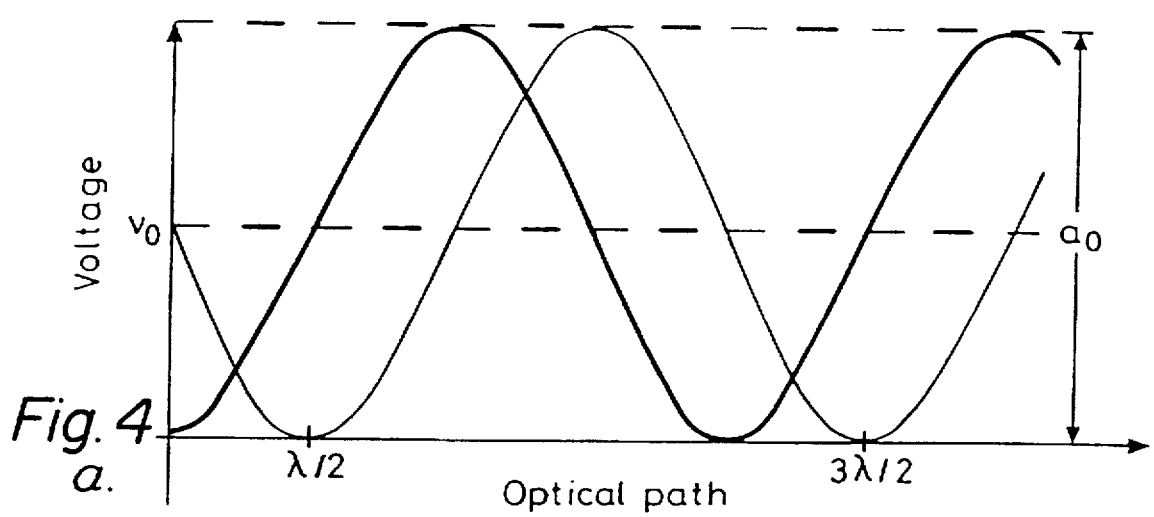
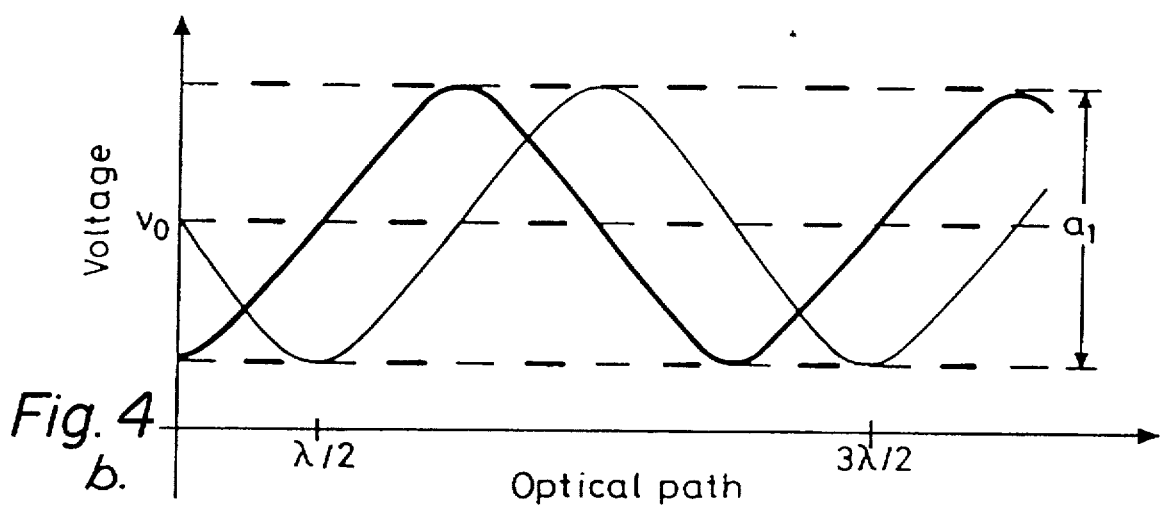
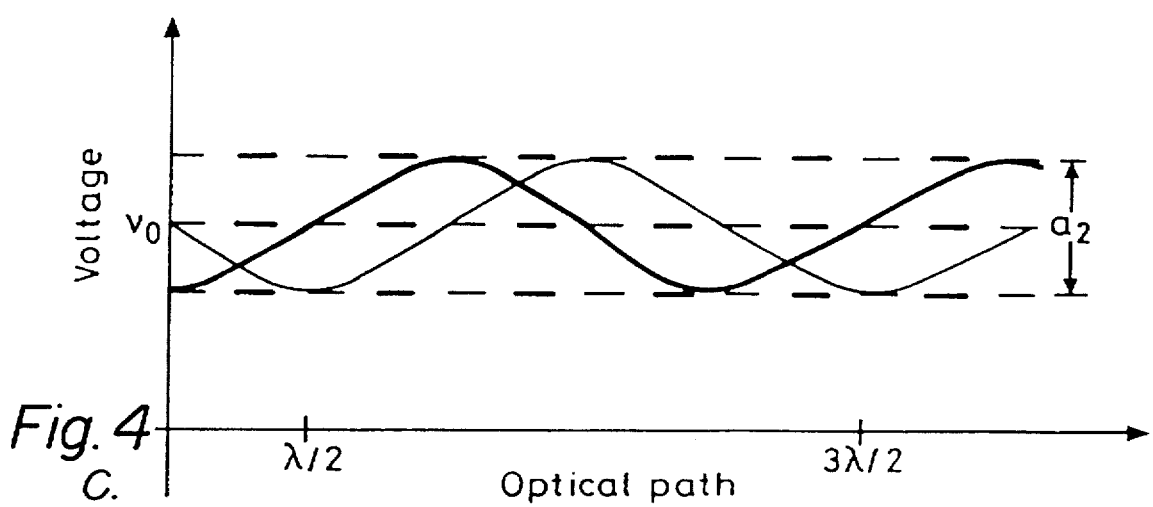
Fig. 4 a.
Fig. 4 b.
Fig. 4 c.

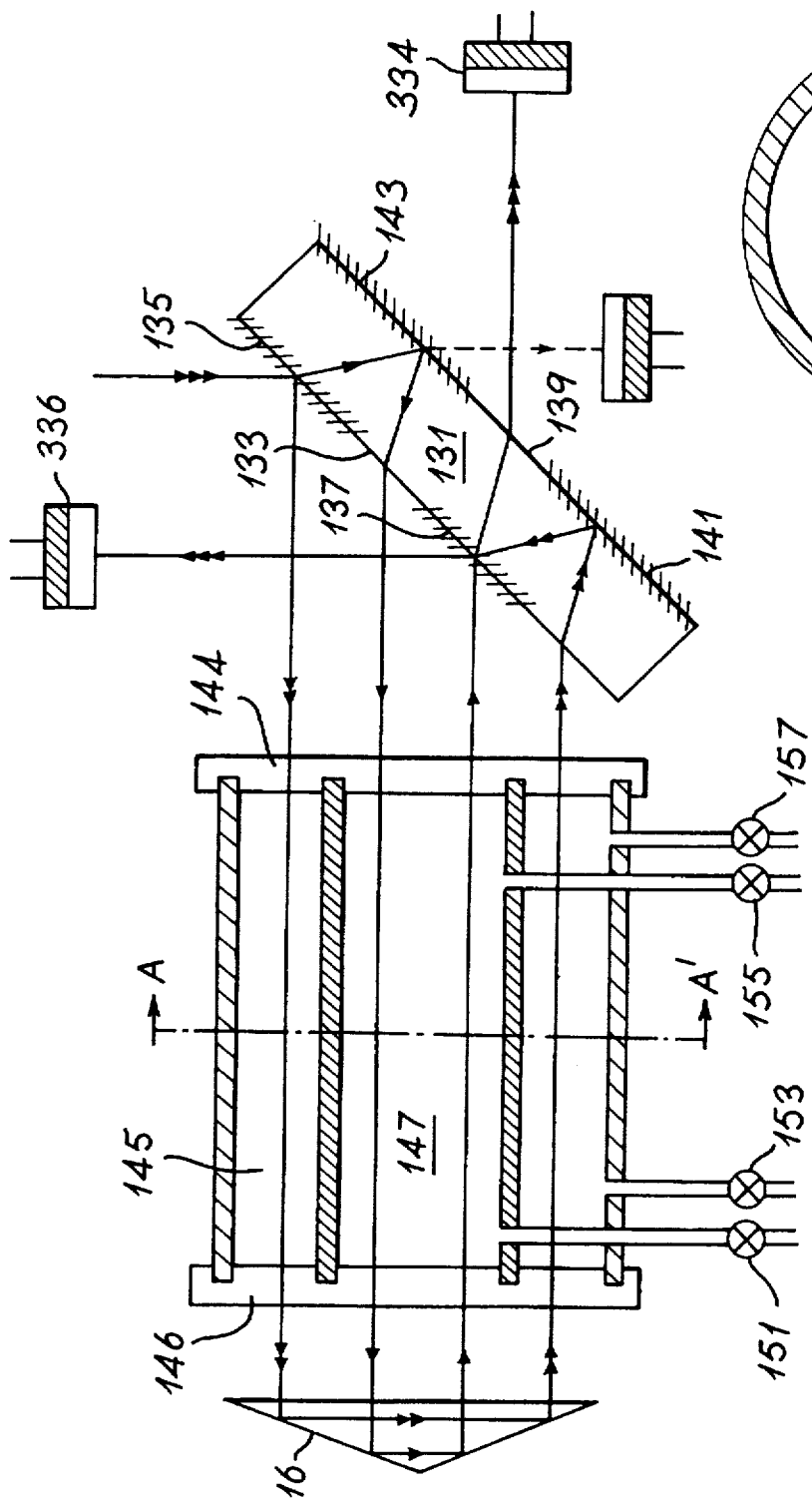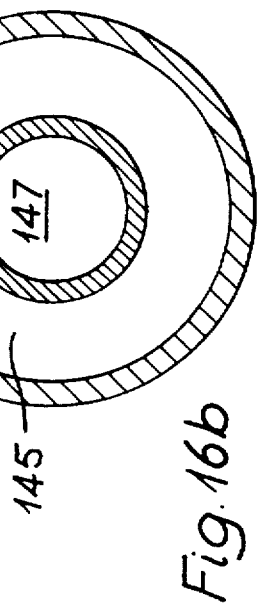
Fig. 16a
Fig. 16b

SINGLE-FREQUENCY BIDIRECTIONAL FRINGE-COUNTING INTERFEROMETER

FIELD OF THE INVENTION

This invention relates to optical measuring instruments and, in particular to a bidirectional fringe-counting two-beam interferometer system.

Stimulated by the development of the 633 nm helium-neon laser in the early 1960's with its intense collimated beam and narrow bandwidth, interferometric length measurement has become one of the most widely implemented techniques of precision measurement. It is used for measurements of length ranging from less than a micrometer, to distances of tens of meters. For the highest accuracy (approaching 1 part in $10^9$, the laser source must be stabilized in frequency and calibrated by comparison with a reference laser and, where the measurement application is in the free atmosphere, it is essential to continuously to correct the wavelength of the radiation for the refractive index of the air. Over shorter distances where a high measurement precision is required, it is necessary to resolve fractions of an optical fringe. In these applications unwanted reflections and polarization effects become fundamental limitations as they cause fringe distortion and limit the fidelity of the electronic signals.

BACKGROUND OF THE INVENTION

Bidirectional counting techniques are used to correct automatically for vibration or retraced motion ensuring that the fringe count represents the displacement of the moving reflector. For optimum performance bi-directional counters require two signals with constant average dc levels and sinusoidal components, related to the optical path difference in the interferometer, that are in phase quadrature. The counter logic is set to respond each time one of the signals passes through its average value. Unfortunately, in practice this dc level is subject to variations. For example, its value is dependent on the intensity of the light source. Removal of the dc component by capacitance coupling, so that the average signal level is always zero, is not completely effective because the frequency of the sinusoidal component may be very low and, indeed, zero if the corner cube retro-reflector attached to the workpiece is stationary.

It is common practice either to employ some form of modulation of the interferometer signal or to maintain the average signal level at zero volts by an electronic subtraction process which removes variations in the average signal level from the photodetector signals and avoids the need for modulation. However, instruments using these methods involve the use of polarization techniques, introducing a 90° phase difference between the signals obtained from two orthogonally polarized components by means of a phase retardation plate. This results in the imposition of alignment requirements on the polarization azimuths of the optical components in the interferometer system and the radiation source and in addition increases the overall cost.

SUMMARY OF THE INVENTION

It is an object of the invention to provide a bidirectional fringe-counting two-beam interferometer system that can be used for precision length measurement with any laser source that is adequately coherent for the application and with any orientation of polarization of the input laser beam.

According to the invention a single frequency bidirectional fringe-counting interferometer system comprises an optical source to provide a single frequency optical beam;

beamsplitter means to divide the optical beam into a reference beam and a measuring beam, the beams having a phase difference of substantially 90°;

optical means to provide from the reference beam and the measuring beam two interfering beams having a path length difference related to a displacement to be measured;

two light sensing means arranged one to receive each interfering beam and to provide related electrical signals each having an ac and a dc component, the signals having a difference in phase equal to the phase difference introduced by the beamsplitter means:

signal processing means to process the signals so as:

a) to continuously to sense their phase difference and when required to modify it to equal 90°;

b) to continuously to sense the rate of change of the path length difference and to compare it with a preset rate of change and when the sensed rate exceeds the preset rate to subtract the respective dc components from the two signals;

c) to continuously to compare the magnitudes of the ac components of the signals and when they are not equal to normalize the ac components; and d) to store the adjustments made;

fringe counting and fractioning means; and display means to provide displays related to the displacement and the fringe fraction.

Preferably, before each measurement of path length difference, the system is initially calibrated by sensing the phase difference of the signals and modifying it to equal 90°.

Optionally the phase difference of the signals is modified by signal addition and signal subtraction and normalization of the ac components of the signals.

Optionally the interferometer system is operable in a first regime in which the path length difference varies at a relatively high counting rate and the system is ac coupled; and is operable in a second regime in which the path length difference varies at a counting rate which is low enough to be digitized and the system is dc coupled.

Preferably the optical source is a laser having a short-term power output variation of less then 2%, such as a polarized helium-neon laser.

The optical means may comprise a Michelson interferometer, or a Jamin interferometer, which may be a gas refractometer.

Optionally the beamsplitter means comprises a partially reflecting metallic film, for example a three layer stack comprising a 4 nm thick chromium layer overcoated with a 16 nm thick film of gold and then a further thick film of chromium between 5 and 6 nm thick.

We have devised a system according to the invention which uses a microprocessor system in conjunction with analogue electronics to automatically and continuously adjust the mean dc level when the path length in the interferometer is changing, and to maintain it at an appropriate value as soon as the signal frequency falls below an adjustable threshold level.

If the average signal level is maintained at a constant value then incomplete interference in the system due to a mis-match in the amplitudes, wavefronts and diameters of the interfering beams, and any non-overlapping of the beams, results in a reduction in contrast and consequently a reduction in the amplitudes of the path length signals with their mean dc levels unchanged enabling the optimum performance to be achieved from the fringe counting and fractioning electronics. However, it will be appreciated that the technique of 'remembering' the required dc voltage level does not compensate for variations in the light source intensity and care must be taken if accurate path length measurement is to be achieved when resolving with nanometric sensitivity by analyzing the interferometer signals. Periodic use of the instrument for measurement, for example, would enable the system to recalibrate itself and correct for any intensity changes that may have occurred during the period the retro-reflector was stationary. Multimode and frequency stabilized Helium-Neon lasers typically vary by less than two percent in their output intensity. A 2% change would produce a 'worst case' error in path length measurement of 1.3 nm.

By careful optical design the effects of unwanted reflections can be reduced to an acceptable level and the technique provides an interferometric system which is insensitive to polarization effects and enables accurate fringe fraction to be achieved.

The microprocessor is also used to monitor and record data on the signals conditions in addition to the results of measurements.

BRIEF DESCRIPTION OF THE DRAWINGS

The prior art, and the problems which are solved by the present invention, will be described with reference to FIGS. 1 to 8 of the accompanying drawings in which:

FIGS. 3A–3C, 4A–4C, 5A–5C, 6A, 7A and 7B are graphs showing relative phase of fringes.

Figure 9:
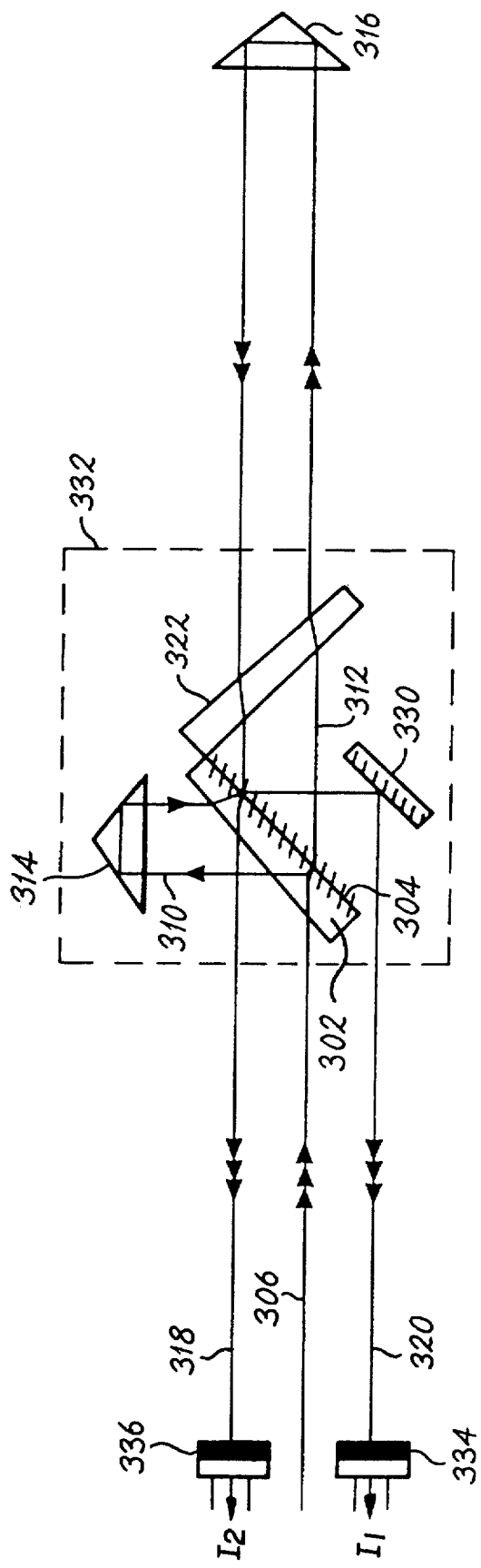
Figure 10:
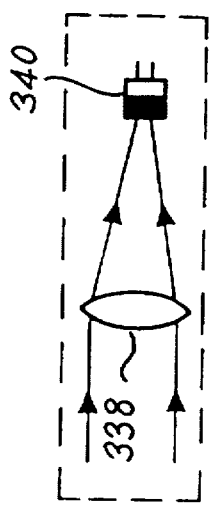
Figure 11:
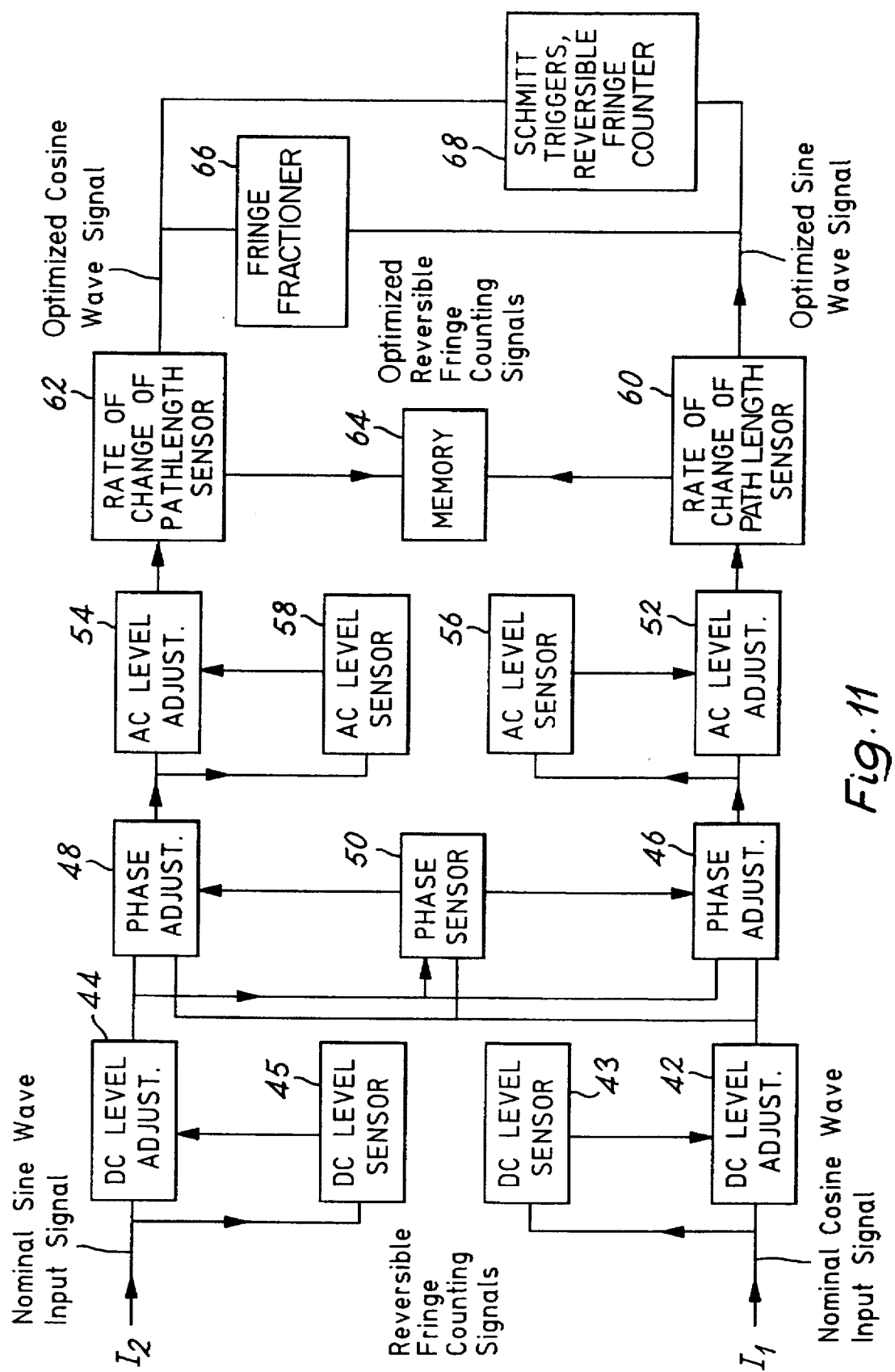
Figure 12:
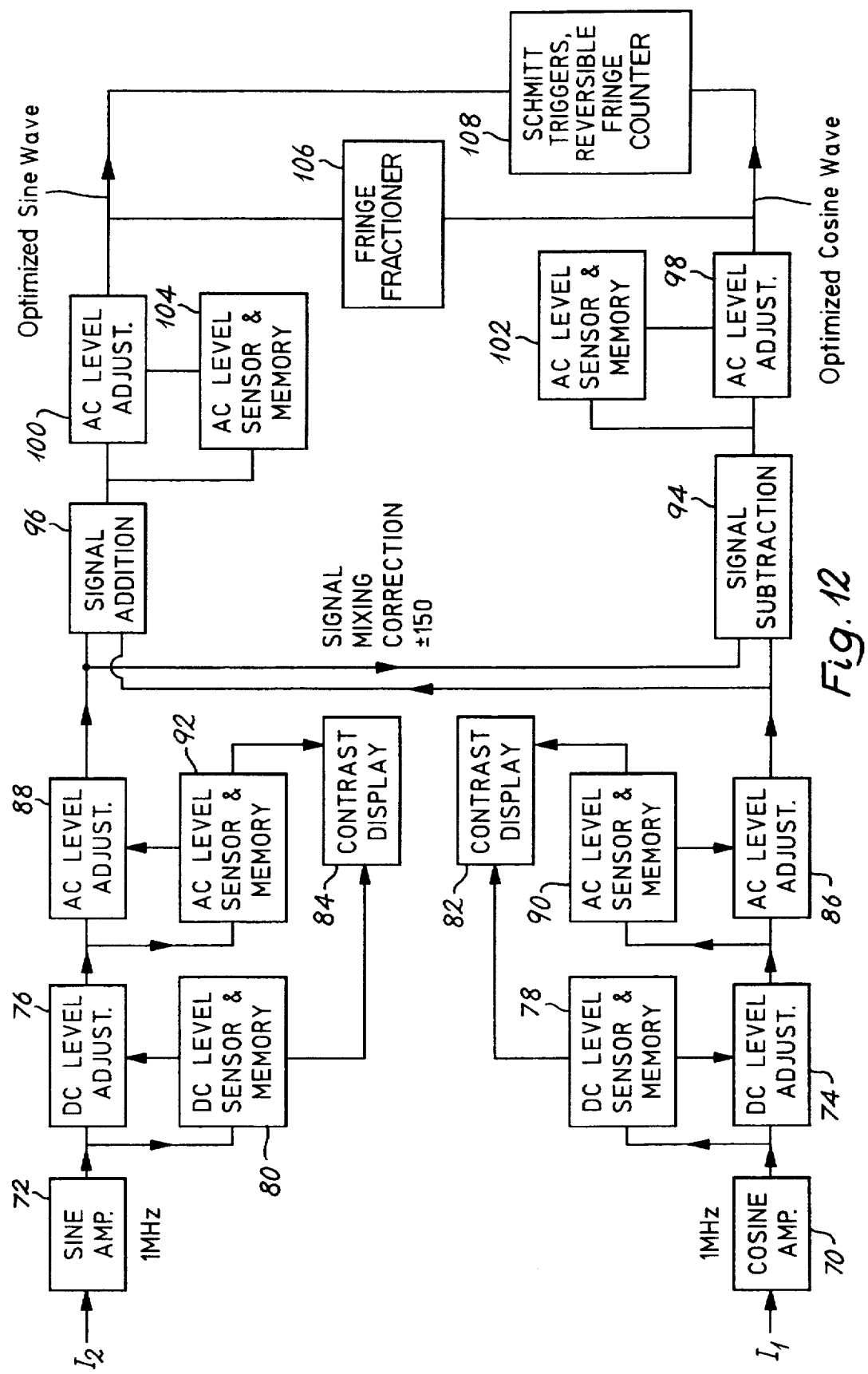

The invention will be described by reference to FIGS. 9 to 21 of the accompanying drawings in which:

FIG. 9 is a schematic view of an interferometer in accordance with a specific embodiment of the present invention;

FIG. 10 is a detail drawing showing a photodetector of the embodiment of FIG. 9;

FIGS. 11 and 12 are block diagrams of signal counting electronic apparatus.

Figure 13:
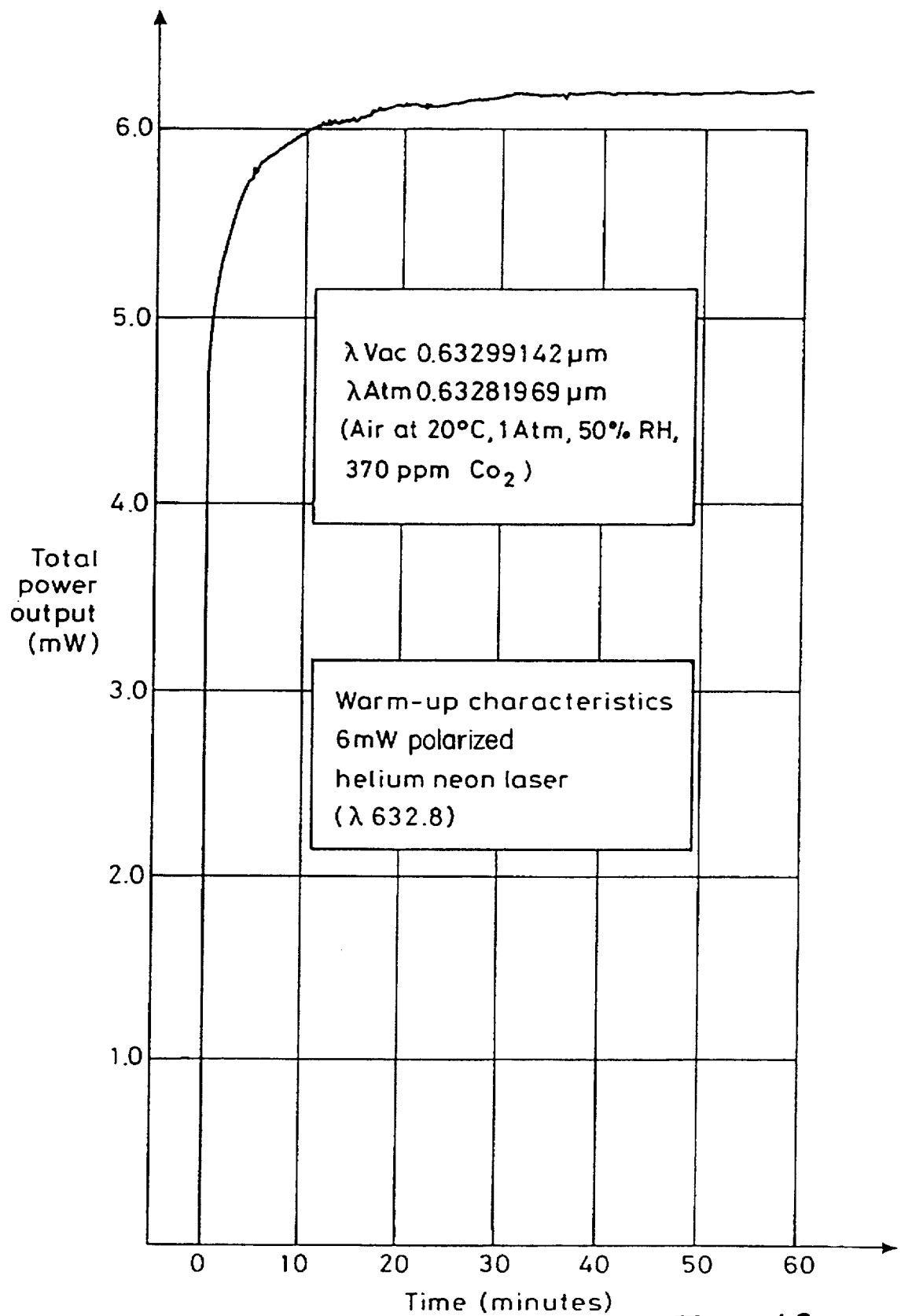
Figure 14:
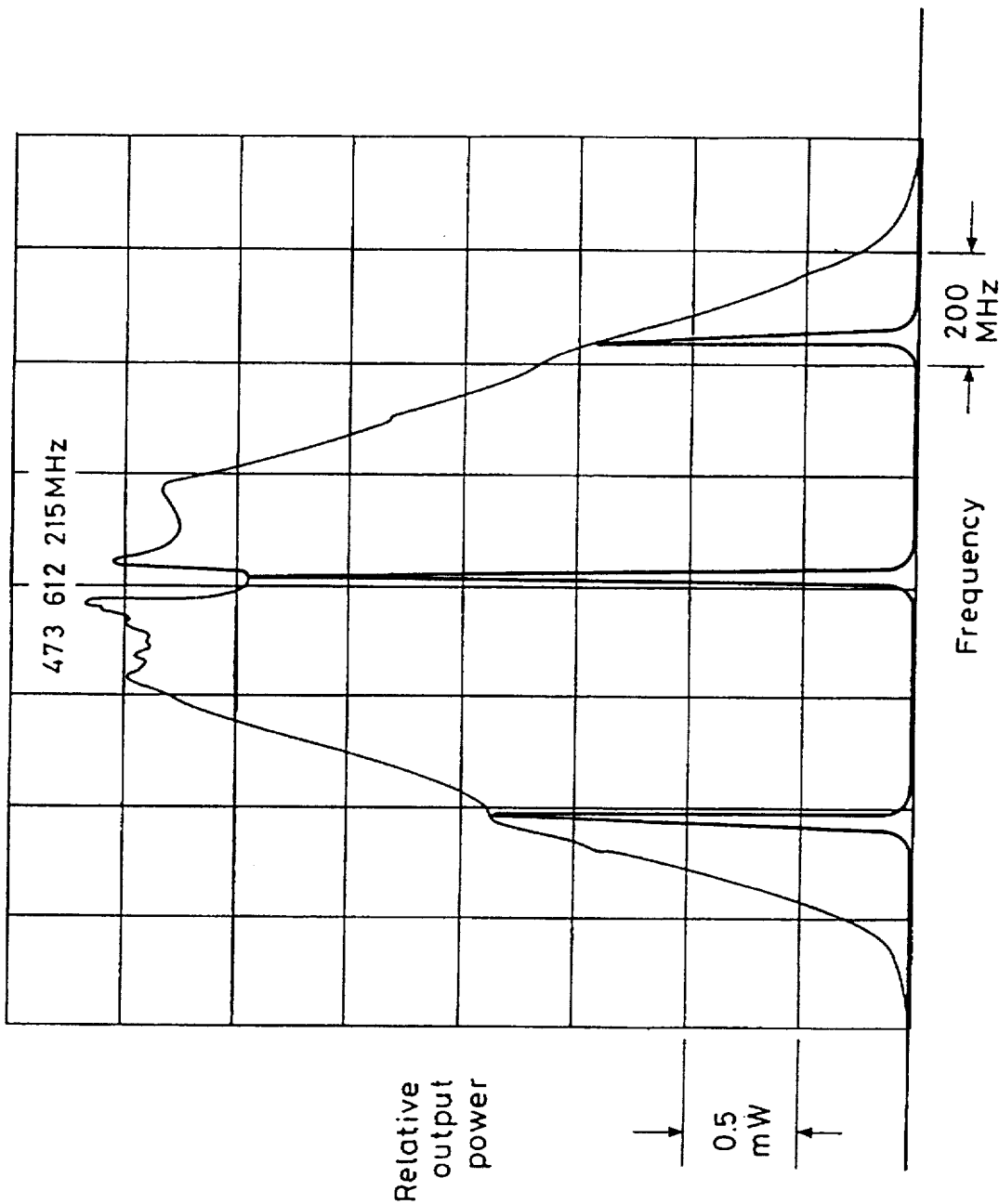
Figure 15:
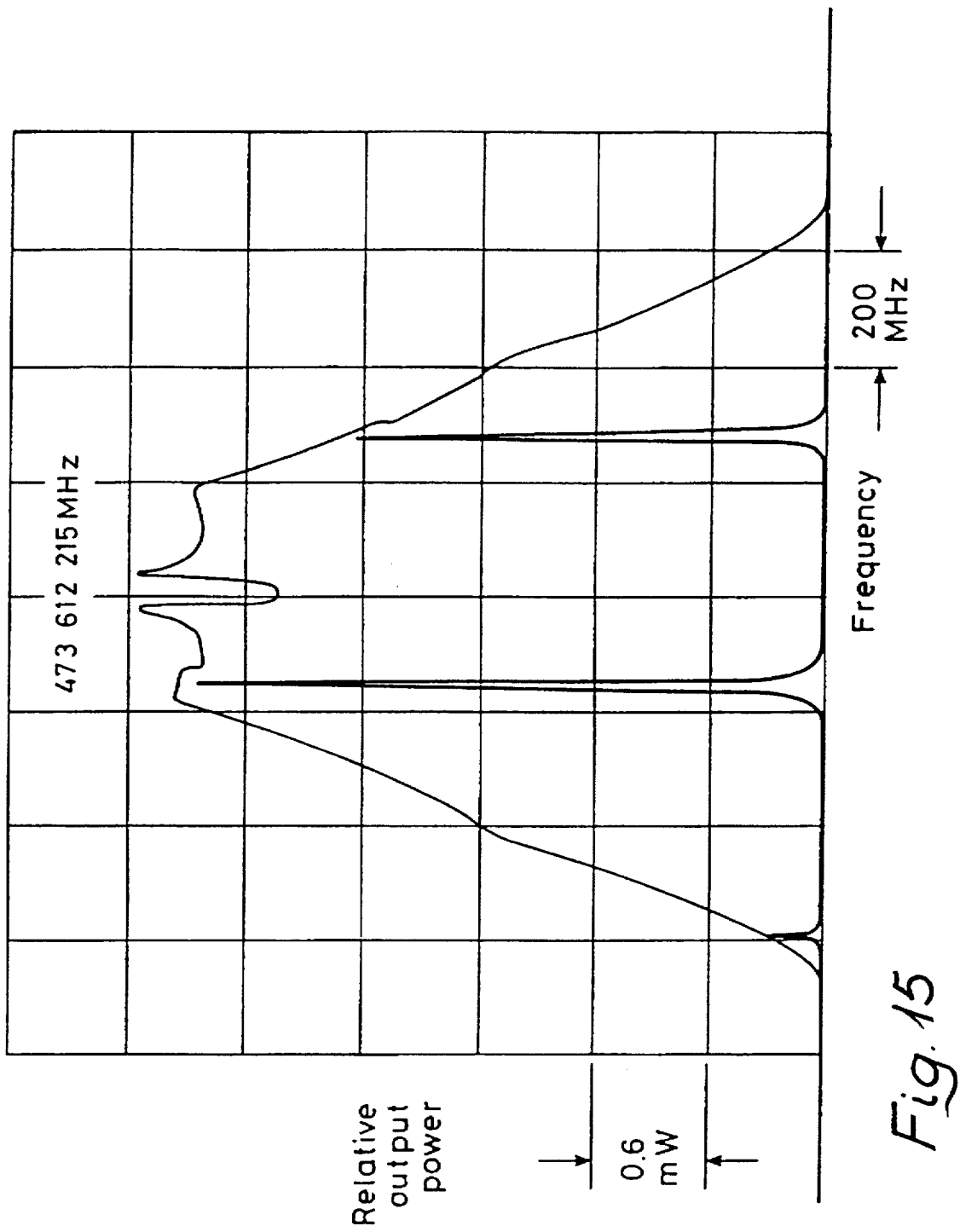
Figure 17:
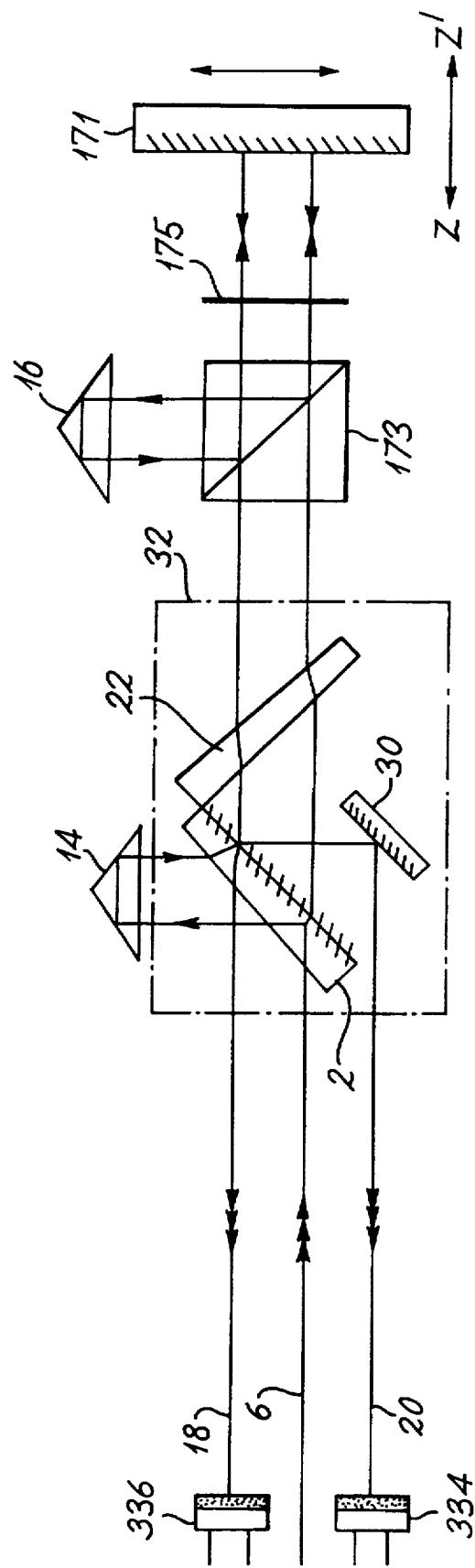
Figure 18:
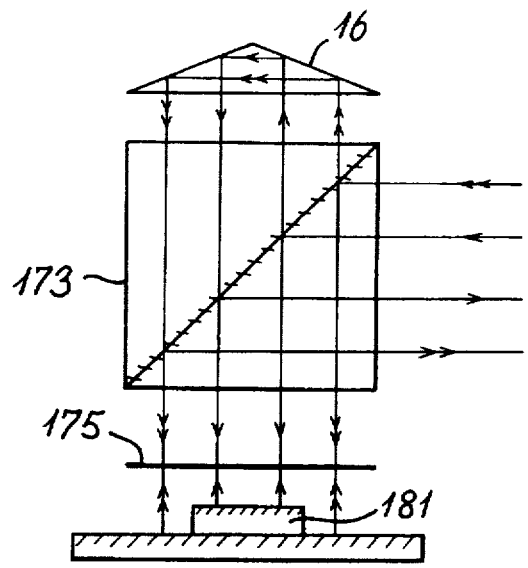
Figure 19:
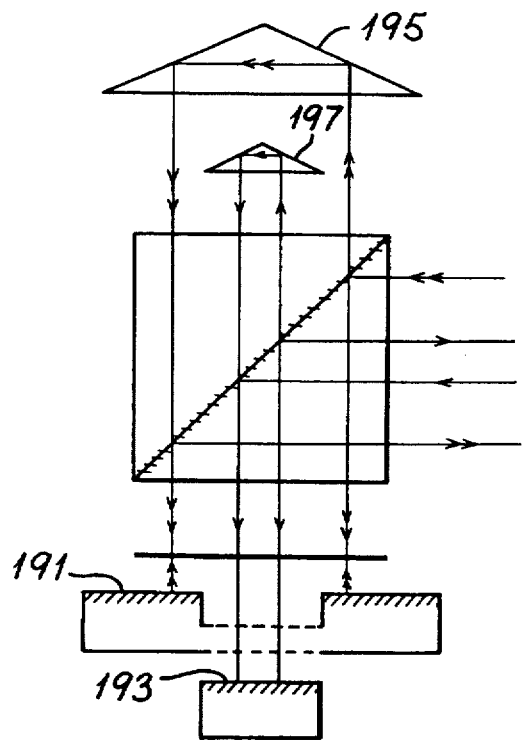
Figure 20:
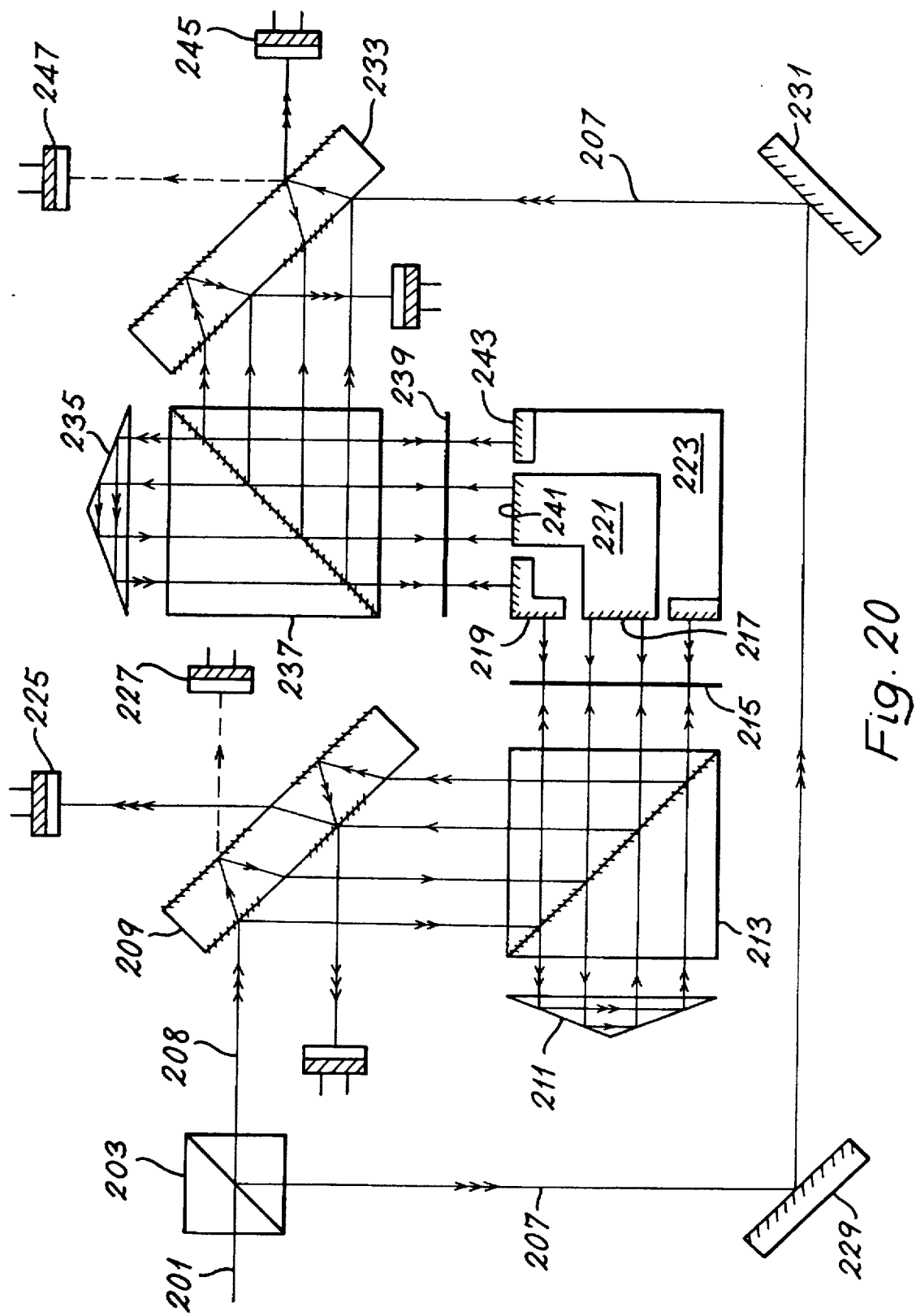

FIGS. 13 to 15 show the output of a He—Ne laser;

FIGS. 16a and 16b are sections showing the optical configuration of an interference gas interferometer;

FIG. 17 shows a modification of the embodiment of FIG. 9;

FIG. 18 is a development of the embodiment of FIG. 16a;

FIG. 19 is a development of the apparatus of FIG. 18;

FIG. 20 shows an application of the embodiment of FIG. 18; and

Figure 21:
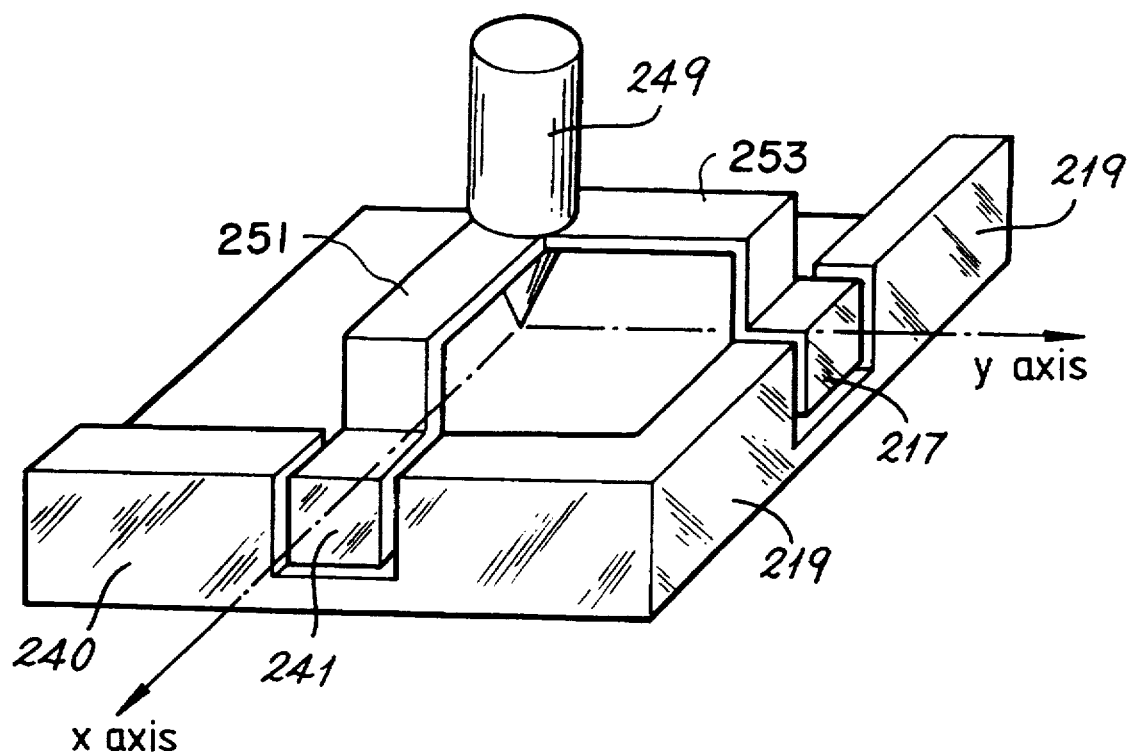

FIG. 21 is a detail of the apparatus of FIG. 20.

DESCRIPTION OF PREFERRED EMBODIMENTS

Figure 1:
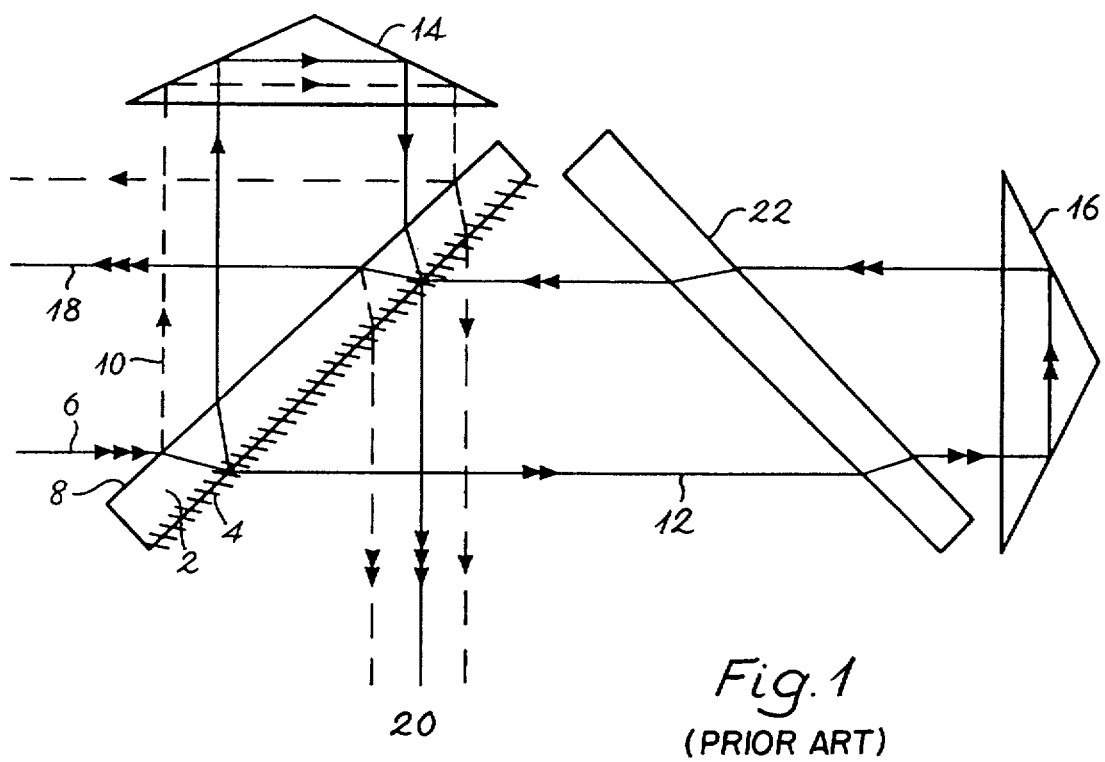
FIG. 1 shows a schematic view of a Michelson interferometer having a wedged compensator plate.
Figure 2:
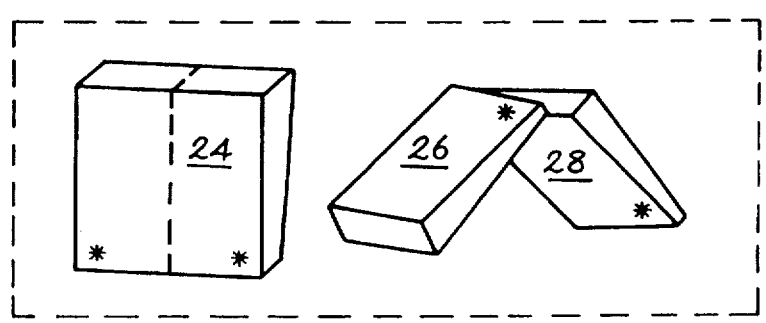
FIG. 2 illustrates the fabrication of the compensator plate of the interferometer of FIG. 1.

A prior art interferometer is illustrated in FIGS. 1 and 2.

The most commonly employed interferometric length measuring systems are based on a design by Michelson and measure displacement in terms of the wavelength of light. In this application the interferometer is made easy to align and insensitive to tilt of the reflecting units by replacing the more conventional plane mirrors with corner cube retro-reflectors. This has the additional advantage of offsetting the return beam and preventing laser instability due to directly reflected radiation entering the laser cavity. One of the corner cubes is fixed with the interferometer beamsplitter, the other is attached to the workpiece under measurement.

In FIG. 1, an optical configuration similar to that employed in the NPL sub-nanometric interferometer described in GB Patent No. 2,235,789. The prior art interferometer comprises an interferometric beamsplitter 2 having a partially reflecting coating 4 on one surface thereof. At the first surface 8 of the beam splitter 2 an incoming laser beam 6 is split into a reference beam 10 and a measuring beam 12. The two separated beams 10,12 are directed towards retro-reflectors 14,16 and further split at the beamsplitter on their return paths, forming two interferograms 18,20. A compensator plate 22 formed from a slightly wedged block is placed in the path of the measuring beam.

Fabrication of the compensator plate is illustrated in FIG. 2. This involves making a slightly wedged beamsplitter plate 24 twice the required dimension which is then cut into two equal parts 26 28. These are orientated with respect to one another in such a way as to compensate for the deviation and displacement they cause in the transmitted beam as shown in FIG. 1. In a practical arrangement, both interferograms are examined remotely from the interferometer block using respective photodetectors (not shown).

The interferometer beamsplitter coating is a three layer metal film stack comprised of a 4 nm thick chromium coating on the substrate overcoated with a 16 nm thick film of gold and then an additional 5 or 6 nm thick film of chromium. This coating design can be readily manufactured using conventional evaporation and monitoring techniques, and produces two signals from the interferometer in phase quadrature to better than % 10° for both the parallel mad perpendicular polarization components.

This design of interferometer has the significant advantage of completely removing the alignment constraints for the polarization azimuths of the system and reducing the optical components required for the interferometer to a plate beamsplitter and two retro-reflectors.

The basic equation for single frequency two beam interferometry is:

$$I = a_1^2 + a_2^2 + 2a_1 a_2 \cos \delta \quad (1)$$

where I=intensity, a=amplitude, δ=optical phase difference given by $\delta = 2\pi(P_1 - P_2)/\lambda$ where P=optical path and λ=wavelength The equation (1) represents a sinusoidal variation of path difference with a peak to peak amplitude of $4a_1 a_2$ superimposed on a mean intensity level of $a_1^2 + a_2^2$. Most bi-directional electronic counters require two electrical signals varying sinusoidally with path length and roughly in phase quadrature with each other, so that the direction of the count may be determined.

In order to operate the logic circuits for counting and direction sensing these signals are fed into the counter inputs through Schmitt trigger circuits. The best performance with regard to reliability, noise immunity and speed of operation, is achieved when the sinusoidal signals are symmetrically disposed about the trigger levels, which are normally set at the mean intensity level (DC level) of the signal. Unfortunately this DC level is subject to variations. For example, its value is dependent on the intensity of the light source and the transmissivities of the optical paths. The fringe counter signals from the interferometer under different conditions are illustrated in FIGS. 3A–3C, 4A–4C, 5A–5C, 6A and 6B.

Figure 3:
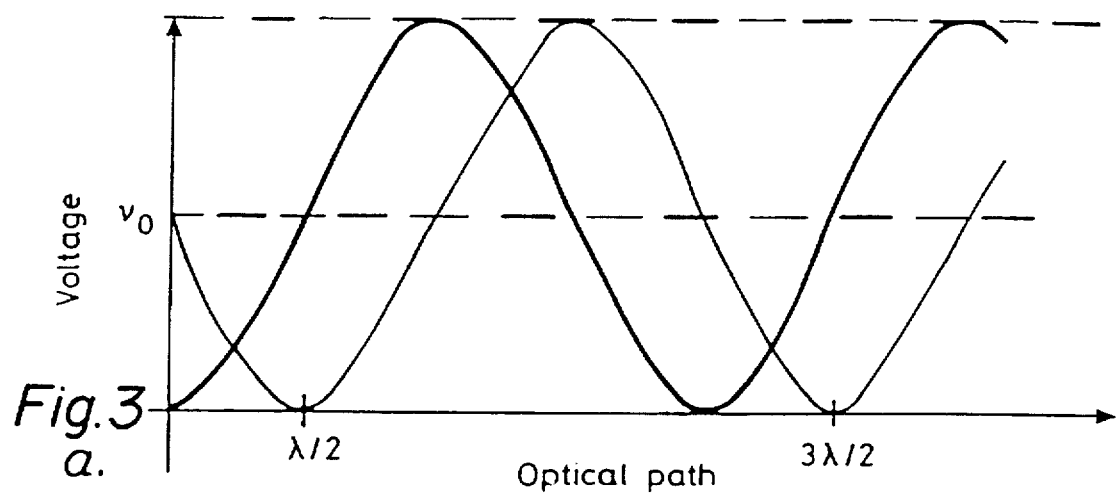
Figure 3:
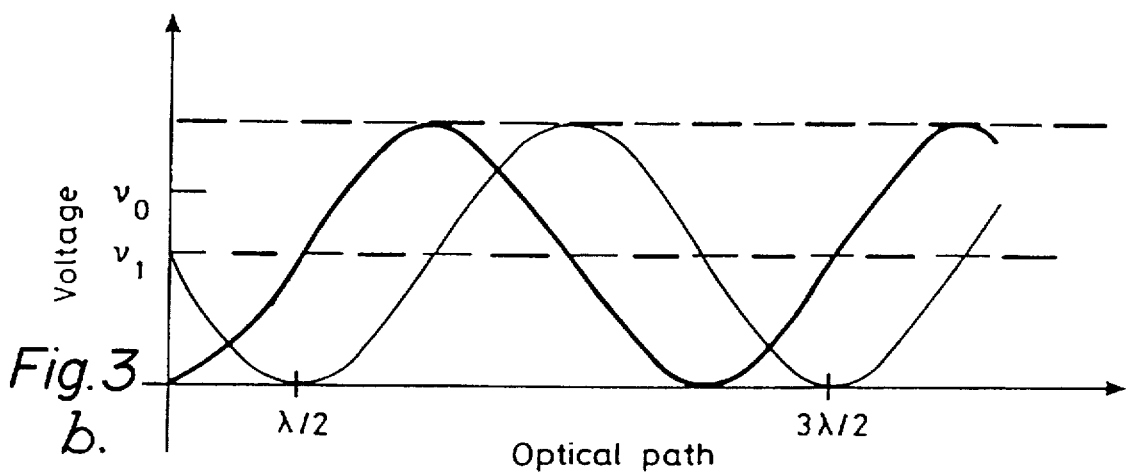
Figure 3:
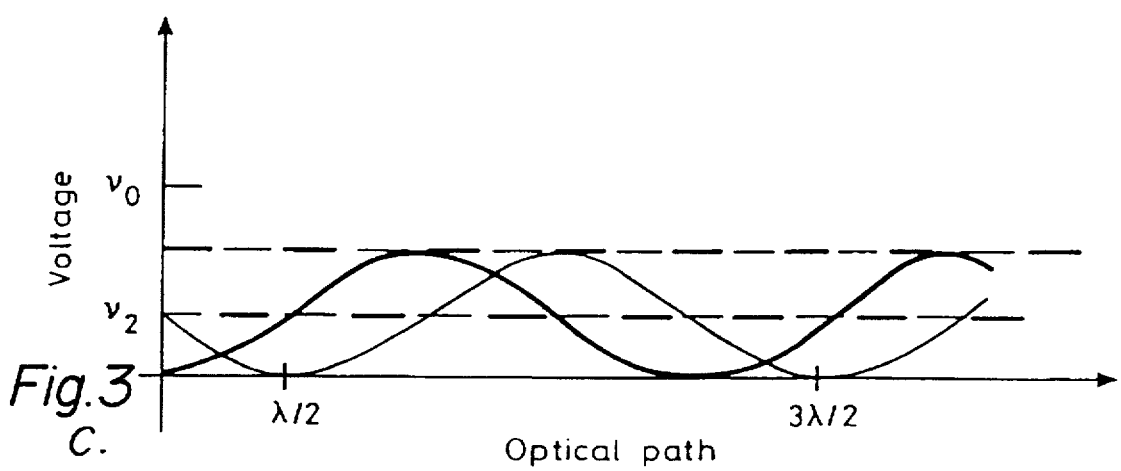

FIG. 3A shows optimized phase quadrature bidirectional fringe counting signals. The signals are sinusoidal and vary symmetrically about a trigger voltage level $V_0$, which is the mean intensity, or the dc level of the signals. FIG. 3B shows two similar phase quadrature signals of reduced amplitude varying about a lower voltage level V, which occurs if, for example, the intensity of the light source decreases, and FIG. 3C shows an even lower amplitude and a greater voltage drop in DC level to voltage $V_2$, i.e, a further fall in intensity.

FIG. 4A shows optimized phase quadrature signals of amplitude $a_0$; FIG. 4B shows two phase quadrature signals of amplitude $a^1$ varying about an unchanged level, and FIG. 4C shows two signals of even further amplitude $a_2$, i.e., further reduced contrast but unchanged DC level $V_0$.

Figure 5:
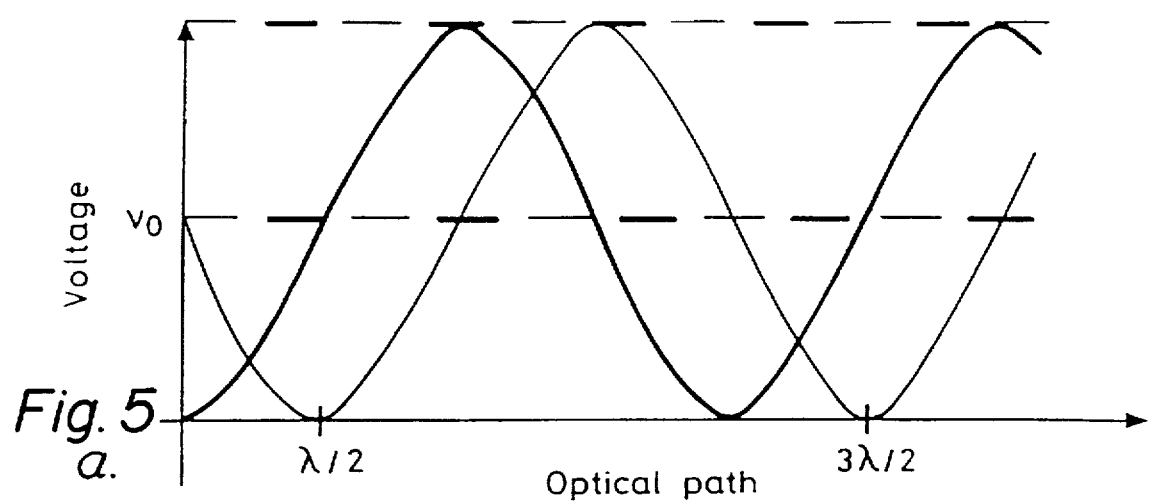
Figure 5:
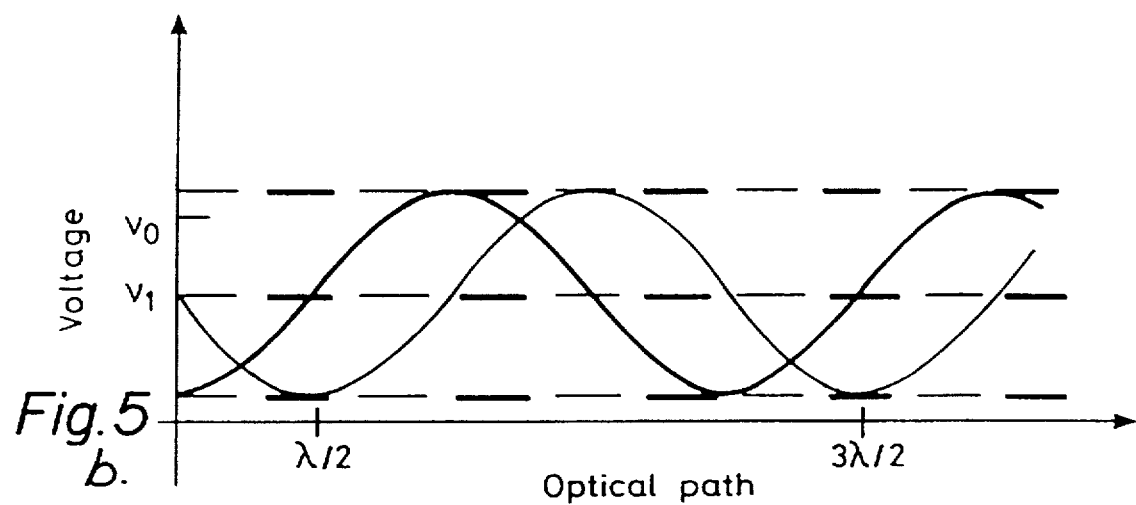
Figure 5:
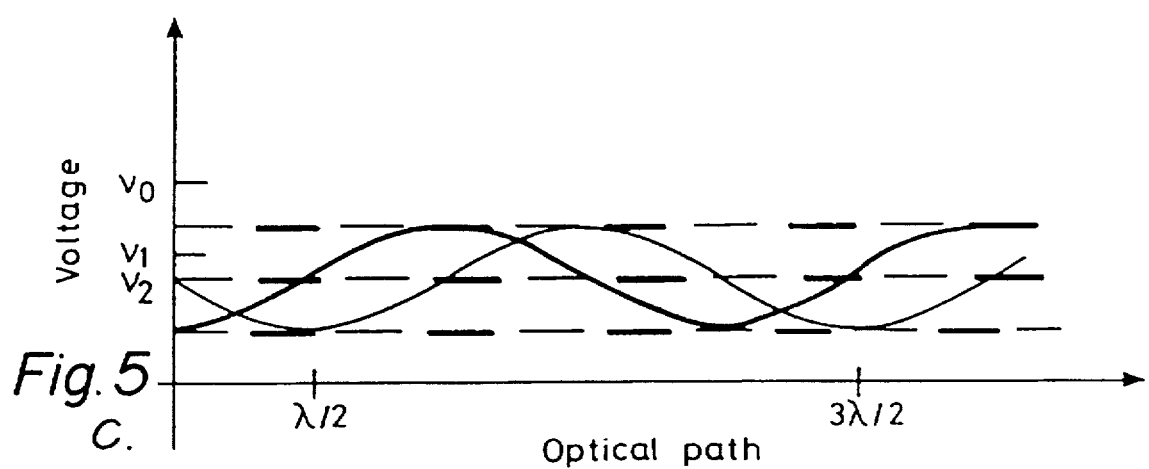

FIG. 5A shows optimized phase quadrature bidirectional fringe counting signals. FIG. 5B shows signals of reduced amplitude varying about a reduced DC level $V_1$ i.e., the combination of the effects of FIGS. 3B and 4B, and FIG. 5C shows a further reduction in amplitude DC level, i.e., the combination of the effects of FIGS. 3C and 4C; i.e. the effect on the interferogram signals of both a decrease in source intensity (the DC level) and a decrease in contrast (the AC level).

The average signal level can be maintained at zero volts by capacitance coupling. However, this technique will only work above a certain threshold frequency for the sinusoidal components.

Figure 6:
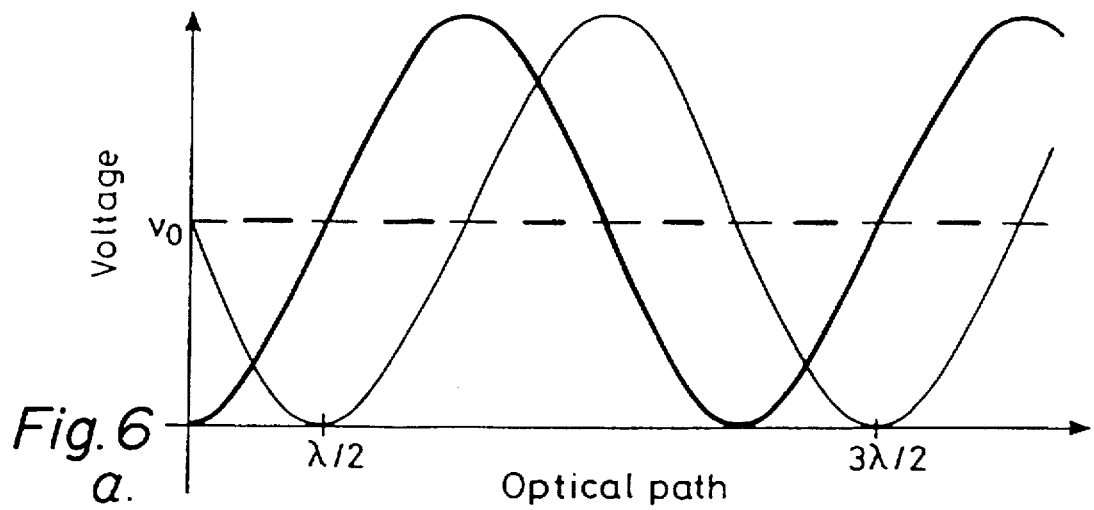
Figure 6:
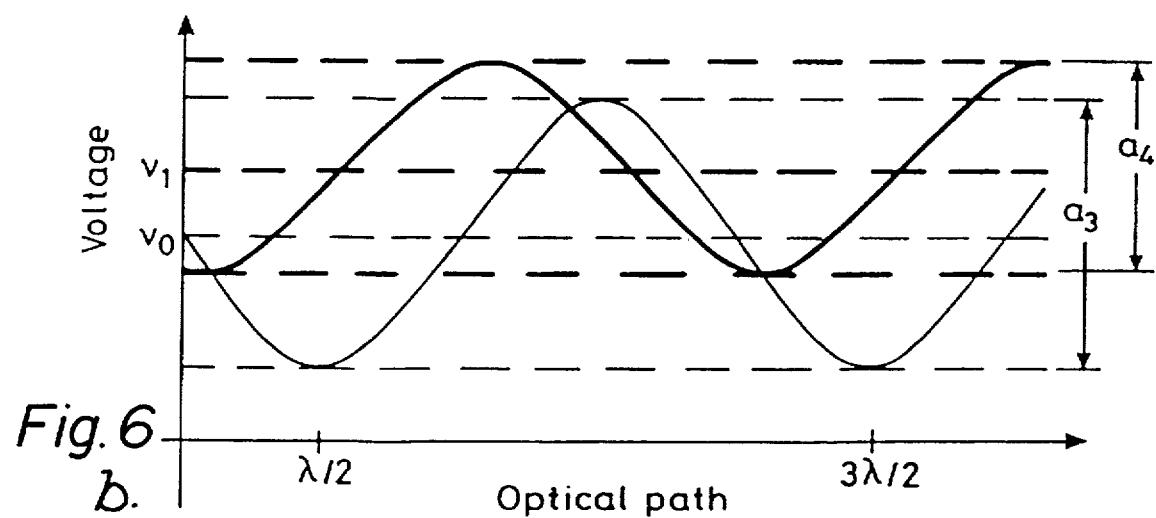

Optimized phase quadrature bidirectional fringe counting signals are shown in FIG. 6A. In practice however the signals obtained by examining the two interferograms of a Michelson interferometer, as shown in FIG. 6B, have different mean intensity levels, different contrast depths and are not perfectly in phase quadrature. The changes in contrast depth that result from differences in the interfering amplitudes are controlled by the optical characteristics of the interferometer beamsplitter. A triple layer gold-chromium film design described above introduces a phase difference of 90±10° between the two interferograms for both the perpendicular and parallel polarisation components and has the reflectance and transmittance values indicated in Table 1. The origin of the reflectances R and transmittances T are illustrated in FIG. 9, which is a simplified version of FIG. 1, indicating only the relevant beam paths.

TABLE 1

| Polarization component | Reflectance | | Transmittance |
|---|---|---|---|
| | $R_s$ | $R_A$ | T |
| P | 25 | 30 | 30 |
| S | 30 | 52 | 16 |

| comp | $R_s^2$ | $T^2$ | contrast depth | $R_sT$ | TRA | contrast depth |
|---|---|---|---|---|---|---|
| P | 6.3% | 9% | 84% | 7.5% | 9% | 91% |
| S | 9% | 2.6% | 54% | 4.8% | 8.3% | 76% |

$R_S$ is the reflectance at the substrate/film interface and $R_A$ the reflectance at the substrate/air interface.

It can be seen from the intensity values that the interfering amplitudes for the interferograms are not matched and that the mean intensity levels of the two interferograms are different.

The invention will now be described by reference to FIGS. 9, 10, 11 and 12. FIG. 9 will be seen by inspection to be optically similar to FIG. 1; optical items having even integers 2 to 22 in FIG. 1 are identical in FIG.9 and are given references advanced by 300.

Figure 7:
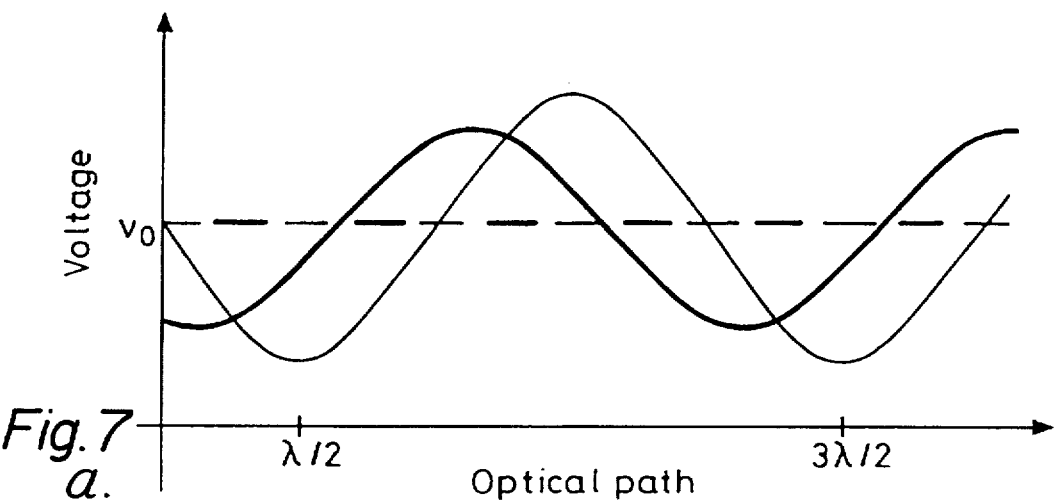
Figure 7:
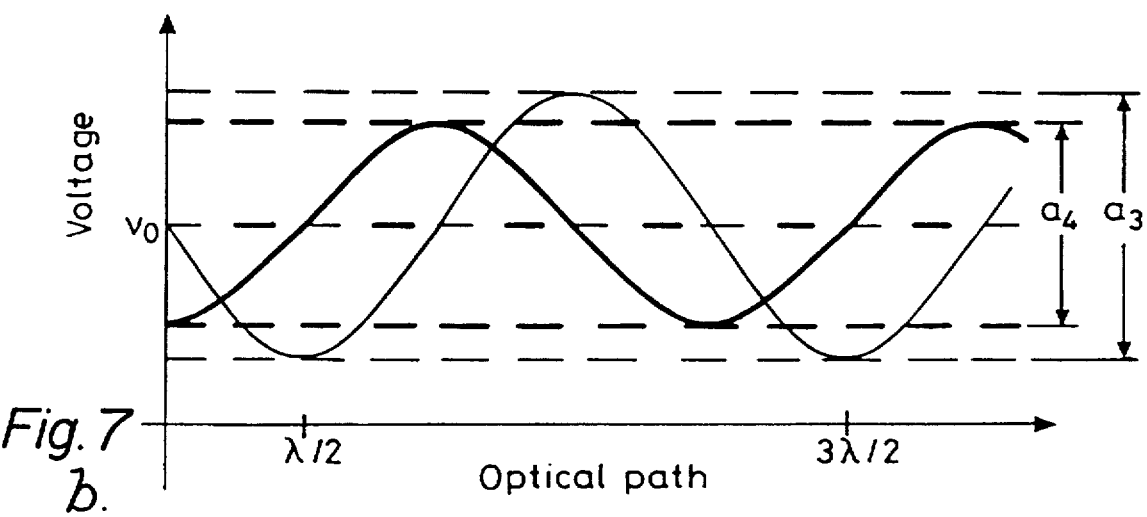
Figure 8:
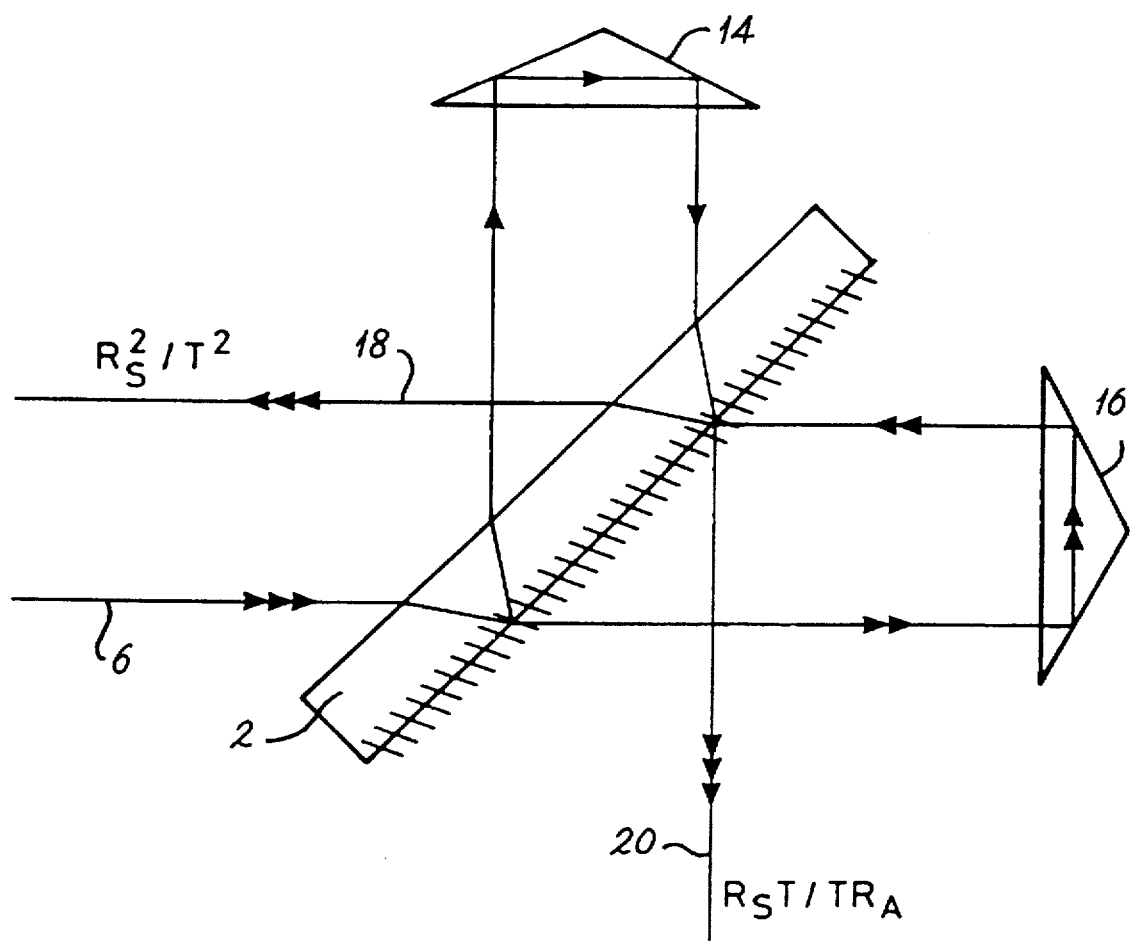
FIG. 8 is a schematic view of a beamsplitter arrangement.

An interferometer comprises an interferometric beamsplitter 302 having a three-layer metallic partially reflecting coating 304 on one surface thereof. An incoming laser beam 306 is split into a reference beam 310 and a measuring beam 312. In this arrangement a reflector 330 is used to enable both interferograms 318, 320 to be examined remotely from the interferometer block 332 using adjacent photodetectors 334, 336. The photodetectors each comprise a lens 338 and photodiode 340 (FIG. 10). The objective is for the poor quality signals shown in FIG. 6B to be connected to a common DC level as shown in FIG. 7A, and additionally connected to be in phase quadrature as shown in FIG. 7B.

For a two-beam interferometer of the type illustrated in FIG. 9, the signals $I_1$ and $I_2$ from the two photodetectors 334, 336 have the form $$I_1 = (a_1^2 + a_2^2) + 2a_1 a_2 \cos(2\pi L/\lambda) \tag{2}$$

$$I_2 = (b_1^2 + b_2^2) + 2b_1 b_2 \cos(2\pi L/\lambda + \phi) \tag{3}$$

where $a_1$ and $a_2$ are the amplitudes of the two components of the recombined beams that reach detector 334, and $b_1$ and $b_2$ are the corresponding amplitudes at detector 336. Each signal varies as a cosine function of the distance L of the moving reflector (e.g. retro reflector 316) relative to an arbitrary origin. The phase difference $\phi$ is due to the properties of the metal beamsplitter coating 304.

In order to determine the value of the distance L from these signals it is advantageous to subtract off the constant terms $(a_1^2 + a_2^2)$ and $(b_1^2 + b_2^2)$, which are dependent mainly upon the reflection/transmission characteristics of the beamsplitter and are proportional to the intensity of the light source. If the gains of the electronic systems amplifying these signals are then adjusted so as to equalise (and normalise) the amplitudes of the alternating signals (making $a_1 a_2 = b_1 b_2$), mad the phase $\phi$ is made equal to 90°, then the signals become:

$$I_1 = \cos(2\pi L/\lambda) \quad I_2 = \sin(2\pi L/\lambda) \tag{3}$$

The distance L can then be determined with an analogue circuit performing the arctangent function in con, junction with a bidirectional counting system that keeps track of the whole number of intensity cycles (each corresponding to a complete $\lambda/2$ increment).

A first example of a circuit to carry out the required adjustments to the electrical signals provided by the detectors 334, 336, is shown in FIG. 11.

The electronic system described below corrects for the residual phase and amplitude variations automatically, and enables the state of polarization employed for the system to be optional and accurate sub-nanometric resolution to be achieved.

The nominal cosine wave input signal $I_1$ (equation 2) is connected to a first DC level adjustment means 42 both directly and through a first DC level sensor 43. Similarly, the nominal sine wave input signal $I_2$ (equation 3, when $\phi=90°$) is connected to a second DC level adjustment means 44 both directly and through a second DC level sensor 45. This part of the circuit operates to subtract off the constant (DC) terms $(a_1^2 + a_2^2)$ and $(b_1^2 + b_2^2)$.

The output signals from the first and second DC level adjustment means 42, 44 are each connected to both first and second phase adjustment means 46, 48 and a phase sensor 50; the phase sensor 50 senses the phase difference between the signals, (which is approximately 90° by reason of the characteristics of the beamsplitter coating 304 in FIG. 9 as explained above). The output of the phase sensor 50 is connected to each phase adjustment means 46, 48 which adjust the phase difference between the two signals to 90°.

The two signals from the phase adjustment means 46, 48 are connected respectively to first and second AC level adjustment means 52, 54, both directly and after passage through respectively first and second ac level sensors 56, 58. This part of the circuit operates to equalize (and normalize) the amplitudes of the alternating signals (making $a_1a_2 = b_1b_2$).

The outputs of the first and second AC level adjustment means 52, 54 are connected respectively to first and second rate of change of path length sensors 60, 62 which each supply one input to a memory 64, and also supply outputs which are respectively an optimized cosine wave signal and an optimized sine wave signal, which are optimized reversible fringe counting signals for supply to conventional fringe fractioning means 66, and to conventional reversible fringe counting means 68 incorporating Schmitt trigger means.

The circuit of FIG. 11 may be implemented by use of a microprocessor.

A partial alterative to the FIG. 11 electrical arrangement is shown in FIG. 12, and may also be implemented by use of a microprocessor. The incoming signals $I_1$, $I_2$ from the detectors 334, 336 are initially amplified in respective amplifiers 70, 72 before passage to first and second DC level adjustment means 74, 76, respectively connected to first and second DC level sensors 78, 80 which in this embodiment each incorporate a DC level memory, and each provide an input to first and second contrast display devices 82, 84.

The AC level adjustment means 86, 88 are connected to AC level sensors 90, 92 which also incorporate AC level memories and each provide one input to the contrast display means 82, 84.

After adjustment of the DC and AC levels, the adjusted signals each supply one input to a signal subtraction means 94 and a signal addition means 96, which supply signal mixing correction, and correct the phase difference between the signals to 90°.

The signals in phase quadrature are now subject to a second adjustment of AC levels by third and fourth AC level adjustment means 98, 100 and associated AC level sensors and memories 102, 104, to provide an optimized cosine wave and an optimized sine wave respectfully. These optimized cosine and sine waves are input to a fringe fractioning means 106 to conventional reversible fringe counting means 108 incorporating Schmitt trigger means.

The system effectively operates in three regimes. If the path length signals are varying rapidly at high counting rates, typically up to 10 MHz on modern counters, the system is phase corrected and AC coupled. At lower frequencies, when the frequency of the path length signal is low enough to be digitized and mathematically analyzed, the system shown in FIG. 11 or FIG. 12 calibrates the phase and signal level corrections required and applies these below this frequency threshold to optimize the signals by adjusting their voltages.

Finally, when the signal frequency falls below a certain threshold the signal level corrections are memorized and held at their respective values. This technique permits accurate fringe fractioning even when the frequency falls to zero when the retro-reflector 316 is stationary.

In addition to maintaining the average signal levels at values generated each time the path length signal falls below a chosen threshold frequency, the FIG. 11 or FIG. 12 system analyzes the signals at this point of time. The phase difference between the signals, their mean DC levels and the amplitudes of the AC path length signals are also calculated and corrections are applied to the signals in order to achieve 'optimized signals' before using an arctangent function to obtain accurate fringe fractioning.

It can be shown from the general equation that if the mean DC levels of the signals are equalized to obtain accurate fringe fractioning from an arctangent function it is necessary to multiply one of the AC path length signals by the ratio of the amplitudes of the sinusoidal path length signals (i.e. $a_4 x a_3/a_4$ as shown in FIG. 7B).

The technique of 'remembering' this ratio, together with the phase and DC level corrections, enables the system to maintain a high level of performance even in the presence of variations of contrast other than those resulting from any intensity changes that occur in the interferometer whilst the retro-reflector is stationary.

When the interferometer is switched on the electronic system of either FIG. 11 or FIG. 12 requires the length signal to be varied once in order to perform the initial calibration and alignment of the system. This process automatically corrects for variations in the optical characteristics of the interferometer beamsplitter effectively broadening its manufacturing tolerances and in addition makes the use of anti-reflection coatings on the optical components optional.

It is common practice with bidirectional fringe counting interferometer systems to introduce 'back-lash' into the Schmitt trigger circuits used at the counter inputs to ensure that no false counts are generated by random noise on the counting signals. The system shown in FIG. 11 or FIG. 12 monitors the fringe count and the fringe fractioning process and ensures that they are always correctly synchronized, and the performance of the total system is continuously and automatically checked. For example, total loss of contrast due to obscuration of one of the beams would result in an alarm being displayed.

The length measuring interferometer system described reduces the optical alignments needed for its operation to the two fundamental requirements for this type of instrument of parallelism between the optical axis of the instrument and the mechanical axis of the measurement stage (cosine error), and coincidence between the measurement point of the system with the measurement direction of the interferometer (Abbe error).

The electronic alignment is totally controlled by the FIG. 11 system or the FIG. 12 system, either of which continuously and automatically processes the two interferometer signals to obtain a high level of performance from the instrument in both accurate fringe counting and fractioning.

In the present design, the adjustment of the signals occurs during every movement which causes the path difference to change faster than a preset rate. Whenever the counting rate is above this rate, the subtracting voltages are separately adjusted in small increments, so as to drive the averaged sinewave signals towards zero volts. These adjustments are halted when the counting rate falls below the preset rate.

In a detailed example (not illustrated) the subtracting voltage changes are carried out at regular intervals by means of ladder resistor networks of the kind used in digital to analogue converters. The settings are 'remembered' and altered by updown counters that are incremented by a clock. A similar arrangement is used to normalise the alternating amplitudes of the signals. In this case the ladder resistor networks alter the feedback ratios of amplifiers, so as to modify their gain. The phase difference between the two signals is adjusted similarly, by altering the mutual mixing of the signals.

However, it will be appreciated that the technique of 'remembering' the required DC voltage level does not compensate for variations in the light source intensity when the rate of change of L in the system falls below the preset rate, and care must be taken if accurate path length measurement is to be achieved when resolving to a nanometer or better. A 2% variation of intensity would produce a 'worst case' error in path length measurement of 1.3 nm. Frequency and intensity stabilized lasers typically have short term power output variations of less than 0.1% and unstabilized multi-mode lasers less than 2%.

In operation, the mechanical system must be 'exercised' before performing any measurements in order to set the system variables. At this point the electronic system tests to confirm that the signal levels and contrast are within acceptable levels, confirming adequate optical alignment. Subsequently during measurements the required adjustments should be small, and any significant departures are monitored to check for partial beam obscuration or other optical disturbances that could indicate dubious measurement conditions.

For test purposes the performance of the system has been evaluated by monitoring the two output voltages of a Michelson interferometer with a computer system. For very slow movements the signals $I_1$ and $I_2$ (Equations (2) and (3)) were read simultaneously with digital voltmeters for many different values of L. The DC and AC levels and the phase term were then determined by a least squares fit. These measurements indicated that the error in each term can easily be kept below 1%, corresponding to periodic errors of less than one nanometer. The resolution of the system in a laboratory environment approached 0.1 nm with a polarized 6 mW unstabilized laser and optical paths of a few centimeters, indicating the exceptional performance that can be achieved by the system.

For the best accuracy, length measuring interferometers use single-mode frequency-stabilized lasers. It is, however, usually unnecessary to use the highest performance iodine frequency-stabilized reference lasers. Such lasers have stabilities of $1\times10^{-11}$ and an absolute frequency for vacuum wavelength accuracy of $1\times10^{-9}$. It is more practical to use Zeeman stabilized or intensity-balance stabilized HeNe lasers that have accuracies between $1\times10^{-8}$ and $1\times10^{-7}$. Alternatively, multimode unstabilized lasers may be used with the proposed system in applications where the optical path difference changes are less than a few centimeters, offering significant cost and reliability advantages. For example, as shown in FIG. 13 the intensity of a polarized 6 mW multimode unstabilized laser is extremely stable after a warm-up time of 30 minutes. FIGS. 14 and 15 show the mode intensities of two samples of such laser. The Doppler-broadened envelopes of the power variations are shown, together with 'snapshot' illustrations of the relative powers and frequencies of the three modes that coexist. These three modes retain their relative separations, but drift across the frequency axis by one mode separation as the laser expands by each g/2 with their power indicated by the envelope. The 'effective' frequency of such a laser is the weighted mean of the three modes, which calculations from these diagrams indicate, varies by less than $1\times10^{-7}$ for all mode positions under the envelope.

Unpolarized lasers are not recommended because although the beamsplitter phase shift is insensitive to the polarisation plane, an unpolarized laser can change its effective polarisation state (e.g. with temperature changes) so quickly that the electronic compensation 'memory' of either FIG. 11 or FIG. 12 would be inadequate.

The electronic systems (FIGS. 11 and 12) continuously and automatically process the two interferometer signals to obtain a high level of performance from the instrument in both accurate fringe counting and fractioning.

An alternative embodiment of the invention employs a Jamin type beamsplitter block 131 as shown in FIGS. 16 and 15b. In this application the front beamsplitter surface 133 is partially coated with a semi-transparent metal film 135, 137 and the back surface 139 with either a fully reflecting coating or, if an intensity reference is required, a reflector with partial transmittance. 141,143. The optical paths of the interference beams pass via windows 144, 146 respectively through outer 145 and inner 147 gas chambers having gas inlet valves 151,153 and gas valves outlet 155,157 valves. The outputs of the detectors 334, 336, provide the inputs to the electronic circuits of FIG. 11 or FIG. 12.

Both the Michelson and Jamin type systems, shown in FIGS. 9 and 16a and 16b can also be used for measuring the displacement of plane mirrors. In these applications it is possible to make the system insensitive to tilting of the mirrors by creating a hybrid retroreflector. This is achieved by employing a cube corner retroreflector, polarizing beamsplitter and λ/4 plate in conjunction with a plane mirror. The polarisation techniques involved in this combination are to improve the coupling efficiency of the combination reflector and do not influence the phase-quadrature adjustment. Poor alignment of the polarising components only results in a drop in contrast, which is automatically corrected for by the electronic system.

FIG. 17 shows a modification to the embodiment of FIG. 9 in which a plane mirror 171 is used for the measurement of displacement in the direction ZZ'. To make the mirror tilt-independent, a polarizing beam splitter 173 and quarter-waveplate 175 are introduced.

The sensitivity is enhanced by the double pass of the mirror.

The air refractometer effectively is a retroreflector common path Jamin interferometer. FIG. 18 shows a dual plain mirror adaptor 181 fitted in place of the retroreflector 16 in the embodiment of FIG. 16a and 16b to form a dilatometer/differential plane mirror interferometer.

In the arrangement of FIG. 19 which is a development of the embodiment of FIG. 18, the dual mirrors 181 are separated and each 191,193 has a corresponding retroreflector 195,197.

A practical application of the arrangement of FIG. 19 is a two-dimensional position measurement device for use with a probe carrier for example for a tunnelling microscope as shown in FIG. 20.

A laser beam 201 is separated by a beamsplitter 203 into two component beams 207,208 used to make X- and Y-measurements. The first component beam 208 passes by way of a first Jamin-type beamsplitter 209 and retroreflector polarizing beamsplitter quarter-waveplate combination 211, 213, 215 to mirrors 217, 219 respectively on a probe carrier 221 and substrate stage 223. Measurement of the returning beams is made by means of an interferogram photodetector 225 and an intensity reference photodetector 227. Orthogonal measurements are made by the second component beam 207 reflected by mirrors 229, 231 to a second Jamin-type beamsplitter 233 and retroreflector polarizing-beamsplitter quarter-waveplate combination 235,237, 239 and mirrors 241,243 respectively on the probe 221 carrier and substrate stage 223. Measurement of the returning beams is made by means of interferogram photodetector 245 and an intensity reference photodetector 247.

FIG. 21 is an isometric view of the apparatus and shows a probe holder 249 with mirror arms 251,253 made of Zerodur or other low expansivity material.

With a system of this nature, over a range of 50 mm there is around 1 nm noise per 25 mm due to the atmosphere. This means that it is feasible to use an unstabilized laser such as a diode laser over a 50 mm range.

Whilst embodiments have been described using films of gold and chromium for the quadrature coating, it is also feasible to use other metallic films such as aluminium to obtain the requisite phase delay.

Summarizing, in the two-beam interferometer systems in accordance with specific embodiments of the invention the measurement signals are produced from two optical outputs of the interferometer. The phase difference between these signals of approximately 90° required for bi-directional counting and fringe fractioning is generated by employing a thin metal film design for the beamsplitter coating. This is in contrast to the more normal use of an all dielectric film beamsplitter design and a phase retardation plate to manipulate the phase difference between two orthogonally polarized components of a single optical output. The system described avoids the cost and alignment of all of the components involved in systems employing these polarization techniques. It is insensitive to polarization effects and avoids the cyclic error problems caused by the polarization leakage that affects heterodyne length-measuring interferometers.

All of the electronic adjustments are automatically controlled by the electronic system. These instruments are economical to manufacture and easy to apply in practice, readily achieving sub-nanometric resolution in the measurement of changes in an optical path.

I claim:

1. A single-frequency bidirectional fringe-counting interferometer system comprising:

an optical source to provide a single-frequency optical beam;

beamsplitter means for dividing said optical beam into a reference beam and a measuring beam, a first phase difference between said optical beam and said reference beam being substantially 90°;

optical means for providing two interfering beams from said reference beam and said measuring beam, a difference in respective path lengths of said two interfering beams being related to a displacement to be measured;

two light sensing means, arranged to receive said two interfering beams, for providing two electrical signals related to said two interfering beams, each of said two electrical signals having an AC component and a DC component, a second phase difference between said two electrical signals being substantially equal to said first phase difference;

signal processing means for processing said two electrical signals, said signal processing means including:

means for continuously sensing said second phase difference between said two electrical signals, and for adjusting a phase of at least one of said two electrical signals by a first adjusted phase shift when required so that said second phase difference equals 90°, means for continuously sensing a rate of change of said difference in said respective path lengths, for comparing said sensed rate of change with a preset rate of change, and for subtracting said respective DC components from said two electrical signals when said sensed rate of change exceeds said preset rate, means for continuously comparing magnitudes of said respective AC components of said two electrical signals, and for normalizing said respective AC components of said two electrical signals when said compared magnitudes are not equal, and means for storing said first adjusted phase shift, said DC components of said two electrical signals, and said AC components of said two electrical signals; and fringe counting and fractioning means for fractioning fringes and for counting said fringes formed by said two interfering beams.

2. A single-frequency bidirectional fringe-counting interferometer system according to claim 1, further comprising calibration means for calibrating said system by sensing said second phase difference between said two electrical signals and phase adjusting at least one of said two electrical signals by a second adjusted phase shift so that said second phase difference equals 90°.

3. A single-frequency bidirectional fringe-counting interferometer system according to claim 2, wherein:

said second phase difference between said two electrical signals is adjusted by at least one of signal addition and signal subtraction.

4. A single-frequency bidirectional fringe-counting interferometer system according to claim 3, wherein:

said system is AC coupled in a first operating mode wherein said difference in respective path lengths of said two interfering beams varies at a first fringe frequency counting rate greater than a predetermined fringe frequency counting rate; and said system is DC coupled in a second operating mode wherein said difference in respective path lengths of said two interfering beams varies at a second fringe frequency counting rate less than said predetermined fringe frequency counting rate.

5. A single-frequency bidirectional fringe-counting interferometer system according to claim 4, wherein said predetermined fringe frequency counting rate is greater than 10 MHz.

6. A single-frequency bidirectional fringe-counting interferometer system according to claim 4, wherein:

said system operates in a third mode wherein, when said difference in said respective path lengths of said two interfering beams varies at a third fringe frequency counting rate less than a threshold fringe frequency counting rate, said first adjusted phase shift, said DC components of said two electrical signals, and said AC components of said two electrical signals are maintained at respective constant values.

7. A single-frequency bidirectional fringe-counting interferometer system according to claim 1, wherein said optical source is a laser having a short-term power output variation of less than 2%.

8. A single-frequency bidirectional fringe-counting interferometer system according to claim 7, wherein said short-term power output variation is less than 0.1%.

9. A single-frequency bidirectional fringe-counting interferometer system according to claim 7, wherein said laser is a polarized helium-neon laser.

10. A single-frequency bidirectional fringe-counting interferometer system according to claim 1, wherein said optical means comprises a Michelson interferometer.

11. A single-frequency bidirectional fringe-counting interferometer system according to claim 1, wherein said optical means comprises a Jamin interferometer.

12. A single-frequency bidirectional fringe-counting interferometer system according to claim 11, wherein said Jamin interferometer is a gas refractometer.

13. A single-frequency bidirectional fringe-counting interferometer system according to claim 1, further comprising:
a hybrid retroreflector.

14. A single-frequency bidirectional fringe-counting interferometer system according to claim 13, wherein said hybrid retroreflector comprises:
a cube corner retroreflector;
a polarizing beamsplitter;
a quarter wave plate; and
a plane mirror arranged to provide measurement of said difference in said respective path lengths of said two interfering beams, said arrangement of said plane mirror being insensitive to tilt.

15. A single-frequency bidirectional fringe-counting interferometer system according to claim 1, wherein said beamsplitter means comprises a partially reflecting metallic film.

16. A single-frequency bidirectional fringe-counting interferometer system according to claim 15, wherein said partially reflecting metallic film comprises:
a chromium layer;
a gold film overcoated on said chromium layer; and
a chromium film on said gold film.

17. A single-frequency bidirectional fringe-counting interferometer system according to claim 16, wherein:
said chromium layer is 4 nm thick;
said gold film is 16 nm thick; and
said chromium film is between 5 nm and 6 nm thick.

18. A single-frequency bidirectional fringe-counting interferometer system according to claim 15, wherein said partially reflecting metallic film comprises aluminum.

19. A single-frequency bidirectional fringe-counting interferometer system comprising:
a laser source to provide an optical beam of wavelength $\lambda$;
a beamsplitter to divide said optical beam into a reference beam and a measuring beam, a first phase difference $\phi$ between said optical beam and said reference beam being substantially 90°;
optical means to provide two interfering beams from said reference beam and said measuring beam, a difference L in respective path lengths of said two interfering beams being related to a displacement to be measured;
two photodetectors arranged to receive said two interfering beams and to provide related electrical signals of respective intensities $I_1$, $I_2$ of said two interfering beams, where $$I_1 = (a_1^2 + a_2^2) + 2a_1 a_2 \cos(2\pi L/\lambda)$$

and $$I_2 = (b_1^2 + b_2^2) + 2b_1 b_2 \cos(2\pi L/\lambda + \phi)$$

where $a_1$ and $a_2$ are respective amplitudes of portions of said reference beam and of said measuring beam which comprise a first one of said two interfering beams, and $b_1$ and $b_2$ are respective amplitudes of portions of said reference beam and of said measuring beam which comprise a second one of said two interfering beams;
signal processing means for processing said two electrical signals, said signal processing means including:
means for continuously sensing said first phase difference $\phi$ between said two electrical signals, and for adjusting a phase of at least one of said two electrical signals by an adjusted phase shift when required so that said first phase difference equals 90°,
means for continuously sensing a rate of change of said difference in said respective path lengths, for comparing said sensed rate of change with a preset rate of change, and for subtracting said components $a_1^2 + a_2^2$ from said signal $I_1$ and subtracting said components $b_1^2 + b_2^2$ from said signal $I_2$ when said sensed rate exceeds said preset rate of change,
means for continuously comparing magnitudes of components $a_1 a_2$ and $b_1 b_2$, and for normalizing said components $a_1 a_2$ and $b_1 b_2$ by a normalization amount when said compared magnitudes are not equal, and
means for storing said adjusted phase shift, said subtracted components $a_1^2 + a_2^2$ and $b_1^2 + b_2^2$, and said normalization amount; and
fringe counting and fractioning means for fractioning fringes and for counting said fringes formed by said two interfering beams.

20. A single-frequency bidirectional fringe-counting interferometer system for measuring path length differences in two orthogonal directions comprising:
an optical source to provide a single frequency optical beam;
two beamsplitter means for dividing said optical beam into first and second reference beams and first and second measuring beams, a first phase difference between said first measuring beam and said first reference beam being substantially 90°, and a second phase difference between said second measuring beam and said second reference beam being substantially 90°;
optical means for providing a first pair of interfering beams having respective differences in a first pair of path lengths related to a first of two orthogonal displacements in said two orthogonal directions to be measured, and for providing a second pair of interfering beams having respective differences in a second pair of path lengths related to a second of said two orthogonal displacements in said two orthogonal directions to be measured;
four light sensing means, receiving respectively said first pair of interfering beams and said second pair of interfering beams, a first two of said four light sensing means for providing a respective first pair of electrical signals related to said first pair of interfering beams, and a second two of said four light sensing means for providing a respective second pair of electrical signals related to said second pair of interfering beams, each of said first pair of electrical signals and said second pair of electrical signals having an AC component and a DC component, said first pair of electrical signals having a third phase difference equal to said first phase difference, and said second pair of electrical signals having a fourth phase difference equal to said second phase difference;
first signal processing means for processing said first pair of electrical signals, said first signal processing means including:
first means for continuously sensing said third phase difference between said first pair of electrical signals, and for adjusting a phase of at least one of said first pair of electrical signals by a first adjusted phase shift when required so that said third phase difference equals 90°,
first means for continuously sensing a rate of change of said difference in said respective first pair of path lengths, for comparing said sensed rate of change with a preset rate of change, and for subtracting respective DC components from said first pair of electrical signals when said first sensed rate exceeds said preset rate of change, first means for continuously comparing magnitudes of respective AC components of said first pair of electrical signals, and for normalizing said respective AC components of said first pair of electrical signals when said compared magnitudes are not equal, and first means for storing said first adjusted phase shift, said DC components of said first pair of electrical signals, and said AC components of said first pair of electrical signals;

second signal processing means for processing said second pair of electrical signals, said second signal processing means including:

second means for continuously sensing said fourth phase difference between said second pair of electrical signals, and for adjusting a phase of at least one of said second pair of electrical signals by a second adjusted phase shift when required so that said fourth phase difference equals 90°, second means for continuously sensing a rate of change of said difference in said respective second pair of path lengths, for comparing said sensed rate of change with said preset rate of change, and for subtracting respective DC components from said second pair of electrical signals when said second sensed rate exceeds said preset rate of change, second means for continuously comparing magnitudes of respective AC components of said second pair of electrical signals, and for normalizing said respective AC components of said second pair of electrical signals when said compared magnitudes are not equal, and second means for storing said second adjusted phase shift, said DC components of said second pair of electrical signals, and said AC components of said second pair of electrical signals; and fringe counting and fractioning means for fractioning fringes and for counting said fringes formed by each of said first pair of interfering beams and said second pair of interfering beams.

21. A method of bidirectionally counting fringes in a single-frequency interferometer system to measure a displacement, said method comprising steps of:

providing a single frequency optical beam;

dividing said single frequency optical beam into a reference beam and a measuring beam, a first phase difference between said reference beam and said measuring beam being substantially 90°;

interfering said reference beam and said measuring beam to form two interfering beams having a difference in respective path lengths related to said displacement to be measured;

sensing an intensity of each of said two interfering beams so as to provide two electrical signals related to said intensity of said two interfering beams, each of said two electrical signals having an AC component and a DC component, a second phase difference between said two electrical signals being equal to said first phase difference;

processing said two electrical signals by steps of:

continuously sensing said second phase difference between said two electrical signals, and adjusting a phase of at least one of said two electrical signals by a first adjusted phase shift when required so that said second phase difference equals 90°, continuously sensing a rate of change of said difference in said respective path lengths, and comparing said sensed rate of change with a preset rate of change, and when said sensed rate exceeds said preset rate of change, subtracting respective DC components from said two electrical signals, continuously comparing magnitudes of respective AC components of said two electrical signals, and when said compared magnitudes are not equal, normalizing said respective AC components of said two electrical signals, and storing said adjusted phase shift, said DC components of said two electrical signals, and said AC components of said two electrical signals; and counting and fractioning interference fringes formed by said two interfering beams.

* * * * *